(12) United States Patent
Dermody et al.

(10) Patent No.: US 9,249,195 B2
(45) Date of Patent: Feb. 2, 2016

(54) REOVIRUS VACCINES AND METHODS OF USE THEREFOR

(75) Inventors: Terence S. Dermody, Brentwood, TN (US); Karl W. Boehme, Little Rock, AR (US); Mine Ikizler, Nashville, TN (US); Gregory J. Wilson, Nashville, TN (US); James D. Chappell, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 250 days.

(21) Appl. No.: 13/639,564

(22) PCT Filed: Apr. 4, 2011

(86) PCT No.: PCT/US2011/031086
§ 371 (c)(1),
(2), (4) Date: Jun. 14, 2013

(87) PCT Pub. No.: WO2011/126976
PCT Pub. Date: Oct. 13, 2011

(65) Prior Publication Data
US 2013/0259887 A1    Oct. 3, 2013

Related U.S. Application Data

(60) Provisional application No. 61/321,739, filed on Apr. 7, 2010.

(51) Int. Cl.
| | |
|---|---|
| *C07K 14/14* | (2006.01) |
| *C07K 14/005* | (2006.01) |
| *A61K 39/15* | (2006.01) |
| *A61K 39/21* | (2006.01) |
| *A61K 39/12* | (2006.01) |
| *A61K 39/00* | (2006.01) |

(52) U.S. Cl.
CPC ........... *C07K 14/14* (2013.01); *A61K 39/12* (2013.01); *A61K 39/21* (2013.01); *C07K 14/005* (2013.01); *A61K 2039/5256* (2013.01); *C07K 2319/40* (2013.01); *C12N 2720/12222* (2013.01); *C12N 2720/12243* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

| | | | |
|---|---|---|---|
| 8,293,498 B2 | 10/2012 | Dermody et al. | |
| 2010/0278863 A1* | 11/2010 | Hoeben | C07K 14/005 424/215.1 |

OTHER PUBLICATIONS

Mercier et al. A chimeric adenovirus vector encoding reovirus attachment protein sigma . 1 targets cells expressing junctional adhesion molecule 1. Proc Natl Acad Sci U S A. Apr. 20, 2004;101(16):6188-93. Epub Apr. 12, 2004.*
McConnell et al. Characterization of a permissive epitope insertion site in adenovirus hexon. J Virol. Jun. 2006;80(11):5361-70.*
Chappell et al. Crystal structure of reovirus attachment protein σ1 reveals evolutionary relationship to adenovirus fiber. The EMBO Journal (2002) 21, 1-11.*
"Wilson Lab", Department of Pediatrics a Vanderbilt, May 5, 2009. Retrieved from the Internet: URL:http://pediatrics.mc.vanderbilt.edu/interior.php?mid=5614 [retrieved on Jun. 10, 2011].
Bassel-Duby et al., "Sequence of reovirus haemagglutinin predicts a coiled-coil structure", *Nature*, 315(6018):421-423, 1985.
Bosarge et al., "Genetic immunization with the region encoding the alpha-helical domain of PspA elicits protective immunity against *Streptococcus pneumonia*", *Infection and Immunity*, 69(9):5456-5463, 2001.
Cardoso et al., "Broadly neutralizing anti-HIV antibody 4E10 recognizes a helical conformation of a highly conserved fusion-associated motif in gp41", *Immunity*, 22(2): 163-173, 2005.
Cubillos et al., "Protection against experimental *P. falciparum* malaria is associated with short AMA-1 peptide analogue α-helical structures", *Biochimie*, 84(12):1181-1188, 2002.
Eckhart et al., "Immunogenic presentation of a conserved gp41 epitope of human immunodeficiency virus type I on recombinant surface antigen of hepatitis B virus", *Journal of General Virology*, 77:2001-2008, 1996.
Furlong et al., "Sigma 1 protein of mammalian reoviruses extends from the surface of viral particles", *Journal of Virology*, 62(1):246-256, 1988.
Kobayashi et al., "A plasmid-based reverse genetics system for animal double-stranded RNA viruses", *Cell Host Microbe*, 1:147-157, 2007.
Kobayashi et al., "An improved reverse genetics system for mammalian orthoreoviruses", *Virology*, 398(2):194-200, 2010.
London et al., "Gut mucosal immunization with reovirus serotype 1/L stimulates virus-specific cytotoxic T cell precursors as well as IgA memory cells in Peyer's patches", *J. Exp. Med.*, 165:830-847, 1987.
Luo et al., "Induction of neutralizing antibody against human immunodeficiency virus type I (HIV-I) by immunization with gp41 membrane-proximal external region (MPER) fused with porcine endogenous retrovirus (PERV) p15E fragment", *Vaccine*, 24(4):435-442, 2006.
Major and Cuff, "Effects of the route of infection on immunoglobulin G subclasses and specificity of the reovirus-specific humoral immune response", *J. Virol*, 70:5968-5974, 1996.
Parker et al., "Fine definition of the epitope on the gp41 glycoprotein of human immunodeficiency virus type I for he neutralizing monoclonal antibody 2F5", *J. Virol.*, 75:10906-10911, 2001.
PCT International Preliminary Report on Patentability issued for International Application No. PCT/US2011/031086, mailed Oct. 18, 2012.
PCT International Search Report and Written Opinion issued for International Application No. PCT/US2011/031086, mailed Jul. 8, 2011.

(Continued)

*Primary Examiner* — Stacy B Chen
*Assistant Examiner* — Nick Zou
(74) *Attorney, Agent, or Firm* — Parker Highlander PLLC

(57) ABSTRACT

The present invention provides for modified reoviruses that carry α-helical epitopes from a variety of pathogens, as well as methods of using such modified reoviruses to generate immune responses against those epitopes in hosts.

21 Claims, 5 Drawing Sheets

(56) References Cited

OTHER PUBLICATIONS

Pilon et al., "Anti-prion activity generated by a novel vaccine formulation", *Neuroscience Letters*, 429(2-3):161-164, 2007.

Shen et al., "In vivo gp41 antibodies targeting the 2F5 monoclonal antibody epitope mediate human immunodeficiency virus type I neutralization breadth", *J. Virol.*, 83:3617-3625, 2009.

Taborda et al., "Mapping of the T-cell epitope in the major 43-kilodalton glycoprotein of *Paracoccidioides brasiliensis* which induces a Th-1 response protective against fungal infection in BALB/c mice", *Infection and Immunity*, 66(2):786-793, 1998.

Tai et al., "Prevalence of reovirus-specific antibodies in young children in Nashville, Tennessee", *J. Infect. Dis.*, 191:1221-1224, 2005.

Tendler et al., "A *Schistosoma mansoni* fatty acid-binding protein, Sm14, is the potential basis of a dual-purpose anti-helminth vaccine", *Proc Natl Acad Sci USA*, 93(1):269-273, 1996.

Tyler et al., "Protective anti-reovirus monoclonal antibodies and their effects on viral pathogenesis", *J. Virol.*, 67:3446-3453, 1993.

Ura et al., "Designed recombinant adenovirus type 5 vector induced envelope-specific CD8(+) cytotoxic T lymphocytes and cross-reactive neutralizing antibodies against human immunodeficiency virus type 1", *J. Gene Med.*, 11:139-149, 2009.

Virgin et al., "Monoclonal antibodies to reovirus reveal structure/function relationships between capsid proteins and genetics of susceptibility to antibody action", *J. Virol.*, 65:6772-6781, 1991.

Wang et al., "M cell DNA vaccination for CTL, immunity to HIV", *Journal Immunology*, 171(9):4717-4725, 2003.

White et al., "Characterization of the adaptive and innate immune response to intravenous oncolytic reovirus (Dearing type 3) during a phase I clinical trial", *Gene Ther.*, 15:911-920, 2008.

Zwick et al., "Broadly neutralizing antibodies targeted to the membrane-proximal external region of human immunodeficiency virus type 1 glycoprotein", *J. Virol.*, 75:10892-10905, 2001a.

Zwick et al., "Neutralization synergy of human immunodeficiency virus type 1 primary isolates by cocktails of broadly neutralizing antibodies", *J. Virol.*, 75:12198-12208, 2001b.

Zwick, "The membrane-proximal external region of HIV-1 gp41: a vaccine target worth exploring", *AIDS*, 19(16):1725-1737, 2005.

\* cited by examiner

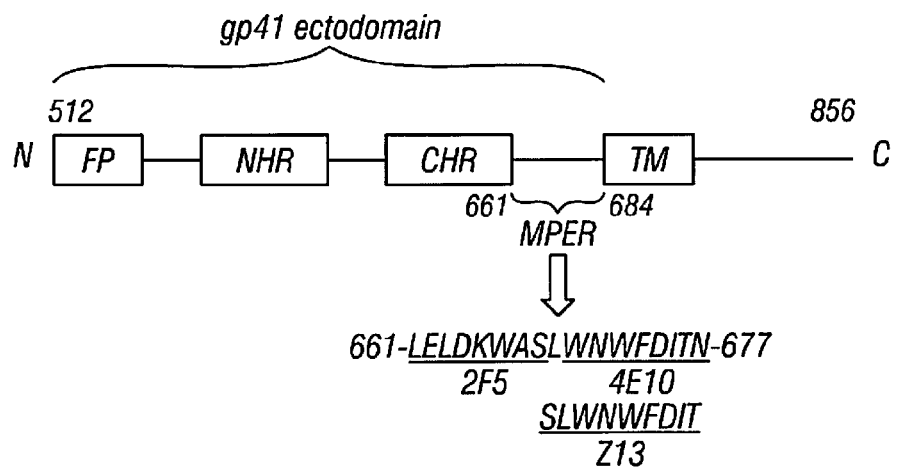
FIG. 1
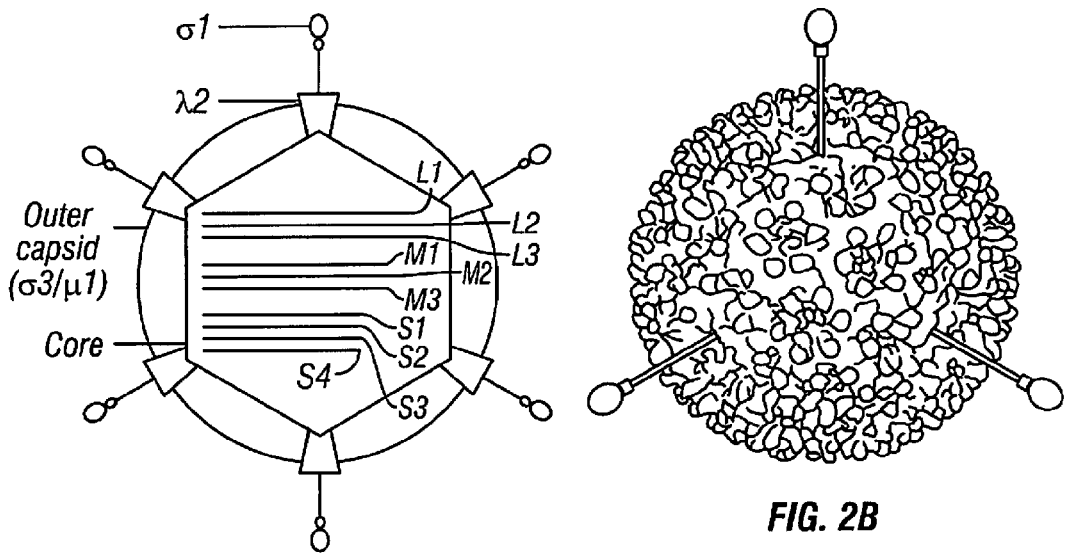
FIG. 2A
FIG. 2B

FIG. 7A — rsT1L σ1

FIG. 7B — rsT1L σ1/2F5-56

FIG. 7C — rsT1L σ1/2F5-154

SEQUENCE LISTING

```
<160> NUMBER OF SEQ ID NOS: 24

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Asn Glu Gln Glu Leu Leu Glu Leu Asp Lys Trp Ala Ser Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Trp Phe Asp Ile Thr Asn Trp Leu
```

<210> SEQ ID NO 3
<211> LENGTH: 55
<212> TYPE: PRT
<213> ORGANISM: Artificial Sequence
<220> FEATURE:
<223> OTHER INFORMATION: Synthetic peptide

<400> SEQUENCE: 3

Ser Met Ser Leu Ala Ser Gly Lys Ser Leu Leu His Glu Val Asp Lys
1               5                   10                  15

Asp Ile Ser Gln Leu Thr Gln Ala Ile Val Lys His Asn Lys Asn Leu
            20                  25                  30

Leu Lys Ile Ala Gln Tyr Ala Ala Gln Asn Arg Arg Gly Leu Asp Leu
        35                  40                  45

Leu Trp Glu Gln Gly Gly Leu
    50                  55

<210> SEQ ID NO 4
<211> LENGTH: 54
<212> TYPE: PRT
<213> ORGANISM: Artificial Sequence
<220> FEATURE:
<223> OTHER INFORMATION: Synthetic peptide

<400> SEQUENCE: 4

Ser Leu Ala Ser Ser Lys Ser Leu Leu Phe Glu Val Asp Lys Asp Ile
1               5                   10                  15

Ser His Leu Thr Gln Ala Ile Val Lys Asn His Gln Asn Ile Leu Arg
            20                  25                  30

Val Ala Gln Tyr Ala Ala Gln Asn Arg Arg Gly Leu Asp Leu Leu Phe
        35                  40                  45

Trp Glu Gln Gly Gly Leu
    50

<210> SEQ ID NO 5
<211> LENGTH: 47
<212> TYPE: PRT
<213> ORGANISM: Artificial Sequence
<220> FEATURE:
<223> OTHER INFORMATION: Synthetic peptide

<400> SEQUENCE: 5

Gln Asp Gly Leu Ile Cys Gly Leu Arg Gln Leu Ala Asn Glu Thr Thr
1               5                   10                  15

Gln Ala Leu Gln Leu Phe Leu Arg Ala Thr Thr Glu Leu Arg Thr Phe
            20                  25                  30

Ser Ile Leu Asn Arg Lys Ala Ile Asp Phe Leu Leu Gln Arg Trp
        35                  40                  45

<210> SEQ ID NO 6
<211> LENGTH: 47
<212> TYPE: PRT
<213> ORGANISM: Artificial Sequence
<220> FEATURE:
<223> OTHER INFORMATION: Synthetic peptide

<400> SEQUENCE: 6

Gln Asn Asn Leu Val Cys Arg Leu Arg Arg Leu Ala Asn Gln Thr Ala
1               5                   10                  15

Lys Ser Leu Glu Leu Leu Phe Arg Val Thr Thr Glu Glu Arg Thr Phe

```
                    20                  25                  30

Ser Leu Ile Asn Arg His Ala Ile Asp Phe Leu Leu Gln Arg Trp
        35                  40                  45

<210> SEQ ID NO 7
<211> LENGTH: 58
<212> TYPE: PRT
<213> ORGANISM: Artificial Sequence
<220> FEATURE:
<223> OTHER INFORMATION: Synthetic peptide

<400> SEQUENCE: 7

Gly Ser Ile Ala Ser Gly Ile Ala Val Ser Lys Val Leu His Leu Glu
1               5                   10                  15

Gly Glu Val Asn Lys Ile Lys Asn Ala Leu Leu Ser Thr Asn Lys Ala
            20                  25                  30

Val Val Ser Leu Ser Asn Gly Val Ser Val Leu Thr Ser Lys Val Leu
        35                  40                  45

Asp Leu Lys Asn Tyr Ile Asn Asn Arg Leu
    50                  55

<210> SEQ ID NO 8
<211> LENGTH: 43
<212> TYPE: PRT
<213> ORGANISM: Artificial Sequence
<220> FEATURE:
<223> OTHER INFORMATION: Synthetic peptide

<400> SEQUENCE: 8

Gly Ser Ser Asp Glu Phe Asp Ala Ser Ile Ser Gln Val Asn Glu Lys
1               5                   10                  15

Ile Asn Gln Ser Leu Ala Phe Ile Arg Arg Ser Asp Glu Leu Leu His
            20                  25                  30

Asn Val Asn Thr Gly Lys Ser Thr Thr Asn Tyr
        35                  40

<210> SEQ ID NO 9
<211> LENGTH: 43
<212> TYPE: PRT
<213> ORGANISM: Artificial Sequence
<220> FEATURE:
<223> OTHER INFORMATION: Synthetic peptide

<400> SEQUENCE: 9

Gly Ser Glu Leu Ser Asn Ile Lys Glu Thr Lys Cys Asn Gly Thr Asp
1               5                   10                  15

Thr Lys Val Lys Leu Ile Lys Gln Glu Leu Asp Lys Tyr Lys Asn Ala
            20                  25                  30

Val Thr Glu Leu Gln Leu Leu Met Gln Asn Thr
        35                  40

<210> SEQ ID NO 10
<211> LENGTH: 43
<212> TYPE: PRT
<213> ORGANISM: Artificial Sequence
<220> FEATURE:
<223> OTHER INFORMATION: Synthetic peptide

<400> SEQUENCE: 10

Leu Glu Ser Glu Val Thr Ala Ile Lys Asn Ala Leu Lys Lys Thr Asn
1               5                   10                  15

Glu Ala Val Ser Thr Leu Gly Asn Gly Val Arg Val Leu Ala Thr Ala
```

```
                20                  25                  30

Val Arg Glu Leu Lys Asp Phe Val Ser Lys Asn
        35                  40

<210> SEQ ID NO 11
<211> LENGTH: 37
<212> TYPE: PRT
<213> ORGANISM: Artificial Sequence
<220> FEATURE:
<223> OTHER INFORMATION: Synthetic peptide

<400> SEQUENCE: 11

Lys Phe Pro Glu Asp Gln Phe Asn Val Ala Leu Asp Gln Val Phe Glu
1               5                   10                  15

Ser Ile Glu Asn Ser Gln Ala Leu Val Asp Gln Ser Asn Arg Ile Leu
            20                  25                  30

Ser Ser Ala Glu Lys
        35

<210> SEQ ID NO 12
<211> LENGTH: 42
<212> TYPE: PRT
<213> ORGANISM: Artificial Sequence
<220> FEATURE:
<223> OTHER INFORMATION: Synthetic peptide

<400> SEQUENCE: 12

Ala Met Lys Asn Ala Asp Asn Ile Asn Lys Leu Lys Ser Ser Ile Glu
1               5                   10                  15

Ser Thr Asn Glu Ala Val Val Lys Leu Gln Glu Thr Ala Glu Lys Thr
            20                  25                  30

Val Tyr Val Leu Thr Ala Leu Gln Asp Tyr
        35                  40

<210> SEQ ID NO 13
<211> LENGTH: 33
<212> TYPE: PRT
<213> ORGANISM: Artificial Sequence
<220> FEATURE:
<223> OTHER INFORMATION: Synthetic peptide

<400> SEQUENCE: 13

Lys Val Asp Ile Ser Ser Gln Ile Ser Ser Met Asn Gln Ser Leu Gln
1               5                   10                  15

Gln Ser Lys Asp Tyr Ile Lys Glu Ala Gln Arg Leu Leu Asp Thr Val
            20                  25                  30

Asn

<210> SEQ ID NO 14
<211> LENGTH: 33
<212> TYPE: PRT
<213> ORGANISM: Artificial Sequence
<220> FEATURE:
<223> OTHER INFORMATION: Synthetic peptide

<400> SEQUENCE: 14

Lys Val Asp Ile Ser Ser Gln Ile Ser Ser Met Asn Gln Ser Leu Gln
1               5                   10                  15

Gln Ser Lys Asp Tyr Ile Lys Glu Ala Gln Lys Ile Leu Asp Thr Val
            20                  25                  30

Asn
```

<210> SEQ ID NO 15
<211> LENGTH: 83
<212> TYPE: PRT
<213> ORGANISM: Artificial Sequence
<220> FEATURE:
<223> OTHER INFORMATION: Synthetic peptide

<400> SEQUENCE: 15

```
Phe Ala Gly Val Val Leu Ala Gly Ala Ala Leu Gly Val Ala Thr Ala
1               5                   10                  15

Ala Gln Ile Thr Ala Gly Ile Ala Leu His Gln Ser Met Leu Asn Ser
            20                  25                  30

Gln Ala Ile Asp Asn Leu Arg Ala Ser Leu Glu Thr Thr Asn Gln Ala
        35                  40                  45

Ile Glu Ala Ile Arg Gln Ala Gly Gln Glu Met Ile Leu Ala Val Gln
    50                  55                  60

Gly Val Gln Asp Tyr Ile Asn Asn Glu Leu Ile Pro Ser Met Asn Gln
65                  70                  75                  80

Leu Ser Cys
```

<210> SEQ ID NO 16
<211> LENGTH: 50
<212> TYPE: PRT
<213> ORGANISM: Artificial Sequence
<220> FEATURE:
<223> OTHER INFORMATION: Synthetic peptide

<400> SEQUENCE: 16

```
Pro Asp Ala Val Tyr Leu His Arg Thr Asp Leu Gly Pro Pro Ile Ser
1               5                   10                  15

Leu Glu Arg Leu Asp Val Gly Ile Asn Leu Gly Asn Ala Ile Ala Lys
            20                  25                  30

Leu Glu Asp Ala Lys Glu Leu Leu Glu Ser Ser Asp Gln Ile Leu Arg
        35                  40                  45

Ser Met
    50
```

<210> SEQ ID NO 17
<211> LENGTH: 83
<212> TYPE: PRT
<213> ORGANISM: Artificial Sequence
<220> FEATURE:
<223> OTHER INFORMATION: Synthetic peptide

<400> SEQUENCE: 17

```
Phe Ala Gly Ile Ala Ile Gly Ile Ala Ala Leu Gly Val Ala Thr Ala
1               5                   10                  15

Ala Gln Val Thr Ala Ala Val Ser Leu Val Gln Ala Gln Thr Asn Ala
            20                  25                  30

Arg Ala Ile Ala Ala Met Lys Asn Ser Ile Gln Ala Thr Asn Arg Ala
        35                  40                  45

Val Phe Glu Val Lys Glu Gly Thr Gln Gln Leu Ala Ile Ala Val Gln
    50                  55                  60

Ala Ile Gln Asp His Ile Asn Thr Ile Met Asn Thr Gln Leu Asn Asn
65                  70                  75                  80

Met Ser Cys
```

<210> SEQ ID NO 18
<211> LENGTH: 52

```
<212> TYPE: PRT
<213> ORGANISM: Artificial Sequence
<220> FEATURE:
<223> OTHER INFORMATION: Synthetic peptide

<400> SEQUENCE: 18

Ser Asn Ile Thr Tyr Ala Glu Asn Leu Thr Ile Ser Leu Ser Gln Thr
1               5                   10                  15

Ile Asn Thr Gln Pro Ile Asp Ile Ser Thr Glu Leu Ser Lys Val Asn
            20                  25                  30

Ala Ser Leu Gln Asn Ala Val Lys Tyr Ile Lys Glu Ser Asn His Gln
        35                  40                  45

Leu Gln Ser Val
    50

<210> SEQ ID NO 19
<211> LENGTH: 133
<212> TYPE: PRT
<213> ORGANISM: Artificial Sequence
<220> FEATURE:
<223> OTHER INFORMATION: Synthetic peptide

<400> SEQUENCE: 19

Pro Phe Ala Met Gln Met Ala Tyr Arg Phe Asn Gly Ile Gly Val Thr
1               5                   10                  15

Gln Asn Val Leu Tyr Glu Asn Gln Lys Gln Ile Ala Asn Gln Phe Asn
            20                  25                  30

Lys Ala Ile Ser Gln Ile Gln Glu Ser Leu Thr Thr Thr Ser Thr Ala
        35                  40                  45

Leu Gly Lys Leu Gln Asp Val Val Asn Gln Asn Ala Gln Ala Leu Asn
    50                  55                  60

Thr Leu Val Lys Gln Leu Ser Ser Asn Phe Gly Ala Ile Ser Ser Val
65                  70                  75                  80

Leu Asn Asp Ile Leu Ser Arg Leu Asp Lys Val Glu Ala Glu Val Gln
                85                  90                  95

Ile Asp Arg Leu Ile Thr Gly Arg Leu Gln Ser Leu Gln Thr Tyr Val
            100                 105                 110

Thr Gln Gln Leu Thr Arg Ala Ala Glu Ile Arg Ala Ser Ala Asn Leu
        115                 120                 125

Ala Ala Thr Lys Met
    130

<210> SEQ ID NO 20
<211> LENGTH: 69
<212> TYPE: PRT
<213> ORGANISM: Artificial Sequence
<220> FEATURE:
<223> OTHER INFORMATION: Synthetic peptide

<400> SEQUENCE: 20

Pro Glu Leu Asp Ser Phe Lys Glu Glu Leu Asp Lys Tyr Phe Lys Asn
1               5                   10                  15

His Thr Ser Pro Asp Val Asp Leu Gly Asp Ile Ser Gly Ile Asn Ala
            20                  25                  30

Ser Val Val Asn Ile Gln Lys Glu Ile Asp Arg Leu Asn Glu Val Ala
        35                  40                  45

Lys Asn Leu Asn Glu Ser Leu Ile Asp Leu Gln Glu Leu Gly Lys Tyr
    50                  55                  60

Glu Gln Tyr Ile Lys
```

```
<210> SEQ ID NO 21
<211> LENGTH: 67
<212> TYPE: PRT
<213> ORGANISM: Artificial Sequence
<220> FEATURE:
<223> OTHER INFORMATION: Synthetic peptide

<400> SEQUENCE: 21

Leu Lys Ser Thr Gln Ala Ala Ile Asp Gln Ile Asn Gly Lys Leu Asn
1               5                   10                  15

Arg Val Ile Glu Lys Thr Asn Glu Lys Phe His Gln Ile Glu Lys Glu
            20                  25                  30

Phe Ser Glu Val Glu Gly Arg Ile Gln Asp Leu Glu Lys Tyr Val Glu
        35                  40                  45

Asp Thr Lys Ile Asp Leu Trp Ser Tyr Asn Ala Glu Leu Leu Val Ala
    50                  55                  60

Leu Glu Asn
65

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Glu Leu Asp Lys Trp Ala Ser Leu
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Leu Glu Leu Asp Lys Trp Ala Ser Leu Trp Asn Trp Phe Asp Ile Thr
1               5                   10                  15

Asn

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Ser Leu Trp Asn Trp Phe Asp Ile Thr
1               5
```

REOVIRUS VACCINES AND METHODS OF USE THEREFOR

This application is a national phase application under 35 U.S.C. §371 of International Patent Application No. PCT/US2011/031086, filed Apr. 4, 2011 which claims benefit of priority to U.S. Provisional Application Serial No. 61/321,739, filed Apr. 7, 2010, the entire contents of which are hereby incorporated by reference.

The invention was made with government support under grant numbers R01 AI32539 and R37 AI38296 awarded by the National Institute of Allergy and Infectious Diseases. The government has certain rights in the invention.

BACKGROUND OF THE INVENTION

1. Field of the Invention

The present invention relates generally to the fields of microbiology, immunology and virology. More particularly, it concerns compositions and methods relating to the use of reovirus-based vaccines containing modified reovirus surface proteins for the immune presentation of non-reovirus epitopes.

2. Description of Related Art

Mammalian orthoreoviruses (reoviruses) are members of the Reoviridae family of viruses. Reoviruses contain 10 double-stranded (ds) RNA gene segments enclosed in two concentric protein shells, outer capsid and core (Nibert and Schiff, 2001). These viruses serve as a versatile experimental system for studies of viral replication events at the virus-cell interface, including engagement of cell-surface receptors (Barton et al., 2001a), internalization and disassembly (Ebert et al., 2002; Ehrlich et al., 2004), and activation of the innate immune response, including NF-κB-dependent cellular signaling pathways (Connolly et al., 2000; O'Donnell et al., 2006). Reoviruses also provide a model system for studies of virus-induced apoptosis and organ-specific disease in vivo (O'Donnell et al., 2005). In addition, genetically-engineered reoviruses are excellent candidates for development of vaccines to elicit protective immunity against a wide variety of pathogens. This is a very appealing idea since reovirus undergoes primary replication in intestinal tissue with few or no symptoms in humans (Tai et al., 2005). However, at present, reovirus has been used as a vaccine platform with only limited success.

SUMMARY OF THE INVENTION

Thus, in accordance with the present invention, there is provided a modified reovirus σ1 protein comprising a first antigenic epitope from a non-reovirus antigen located in the α-helical region of the protein. The first epitope may be inserted into the α-helical region of the protein, or may replace one or more heptad repeats in the α-helical region of the protein.

The first epitope may be a viral epitope, such as from human immunodeficiency virus-1, human immunodeficiency virus-2, human T-cell leukemia virus-1, human T-cell leukemia virus-2, hepatitis B virus, human respiratory syncytial virus, influenza A virus, influenza B virus, influenza C virus, human parainfluenza virus type 1, human parainfluenza virus type 2, human parainfluenza virus type 3, human parainfluenza virus type 4a, human parainfluenza virus type 4b, mumps virus, measles virus, human metapneumovirus, Hendra virus, Nipah virus, Ebola virus, Marburg virus, SARS-associated coronavirus, herpes simplex virus-1, herpes simplex virus-2, varicella-zoster virus, Epstein-Barr virus, human cytomegalovirus, human herpesvirus-6, human herpesvirus-7, or Kaposi's sarcoma-associated herpesvirus. The first epitope may be a bacterial epitope, such as from *Acinetobacter* spp., *Aggregatibacter* spp., *Bartonella* spp., *Brucella* spp., *Burkholderia* spp., *Citrobacter* spp., *Edwardsiella* spp., *Escherichia* spp., *Haemophilus* spp., *Klebsiella* spp., *Legionella* spp., *Moraxella* spp., *Morganella* spp., *Neisseria* spp., *Proteus* spp., *Providencia* spp., *Salmonella* spp., *Serratia* spp., *Shigella* spp., *Staphylococcus* spp., *Stenotrophomonas* spp., *Streptococcus* spp., or *Yersinia* spp. The first epitope may be a fungal epitope, a parasite epitope, or a prion epitope.

The modified reovirus σ1 protein may further comprise a second copy of the first epitope in the α-helical region. The second copy may be adjacent to the first epitope, or distal to the first epitope. The α-helical region may comprise a second epitope distinct from the first epitope. The second epitope may be adjacent to the first epitope, or distal to the first epitope. The second epitope may be from the same antigen as the first epitope, or different antigen as the first epitope. The second epitope may be from the same organism as the first epitope, or from a different organism as the first epitope. The second epitope may be inserted into the α-helical region of the protein, or replace one or more heptad repeats in the α-helical region of the protein.

In another embodiment, there is provided a nucleic acid encoding a modified reovirus σ1 protein comprising a first antigenic epitope from a non-reovirus antigen located in α-helical region of the protein. The first epitope may be inserted into the α-helical region of the protein, or may replace one or more heptad repeats in the α-helical region of the protein.

The first epitope may be a viral epitope, such as from human immunodeficiency virus-1, human immunodeficiency virus-2, human T-cell leukemia virus-1, human T-cell leukemia virus-2, hepatitis B virus, human respiratory syncytial virus, influenza A virus, influenza B virus, influenza C virus, human parainfluenza virus type 1, human parainfluenza virus type 2, human parainfluenza virus type 3, human parainfluenza virus type 4a, human parainfluenza virus type 4b, mumps virus, measles virus, human metapneumovirus, Hendra virus, Nipah virus, Ebola virus, Marburg virus, SARS-associated coronavirus, herpes simplex virus-1, herpes simplex virus-2, varicella-zoster virus, Epstein-Barr virus, human cytomegalovirus, human herpesvirus-6, human herpesvirus-7, or Kaposi's sarcoma-associated herpesvirus. The first epitope may be a bacterial epitope, such as from *Acinetobacter* spp., *Aggregatibacter* spp., *Bartonella* spp., *Brucella* spp., *Burkholderia* spp., *Citrobacter* spp., *Edwardsiella* spp., *Escherichia* spp., *Haemophilus* spp., *Klebsiella* spp., *Legionella* spp., *Moraxella* spp., *Morganella* spp., *Neisseria* spp., *Proteus* spp., *Providencia* spp., *Salmonella* spp., *Serratia* spp., *Shigella* spp., *Staphylococcus* spp., *Stenotrophomonas* spp., *Streptococcus* spp., or *Yersinia* spp. The first epitope may be a fungal epitope, a parasite epitope, or a prion epitope.

The nucleic acid may further comprise a second copy of the first epitope in the a-helical region. The second copy may be adjacent to the first epitope, or distal to the first epitope. The α-helical region may comprise a second epitope distinct from the first epitope. The second epitope may be adjacent to the first epitope, or distal to the first epitope. The second epitope may be from the same antigen as the first epitope, or different antigen as the first epitope. The second epitope may be from the same organism as the first epitope, or from a different organism as the first epitope. The second epitope may be inserted into the α-helical region of the protein, or replace one or more heptad repeats in the α-helical region of the protein.

In yet another embodiment, there is provided a reovirus vector encoding a reovirus σ1 protein comprising a first antigenic epitope from a non-reovirus antigen located in α-helical region of the protein. The first epitope may be inserted into the α-helical region of the protein, or may replace one or more heptad repeats in the α-helical region of the protein.

The first epitope may be a viral epitope, such as from human immunodeficiency virus-1, human immunodeficiency virus-2, human T-cell leukemia virus-1, human T-cell leukemia virus-2, hepatitis B virus, human respiratory syncytial virus, influenza A virus, influenza B virus, influenza C virus, human parainfluenza virus type 1, human parainfluenza virus type 2, human parainfluenza virus type 3, human parainfluenza virus type 4a, human parainfluenza virus type 4b, mumps virus, measles virus, human metapneumovirus, Hendra virus, Nipah virus, Ebola virus, Marburg virus, SARS-associated coronavirus, herpes simplex virus-1, herpes simplex virus-2, varicella-zoster virus, Epstein-Barr virus, human cytomegalovirus, human herpesvirus-6, human herpesvirus-7, or Kaposi's sarcoma-associated herpesvirus. The first epitope may be a bacterial epitope, such as from *Acinetobacter* spp., *Aggregatibacter* spp., *Bartonella* spp., *Brucella* spp., *Burkholderia* spp., *Citrobacter* spp., *Edwardsiella* spp., *Escherichia* spp., *Haemophilus* spp., *Klebsiella* spp., *Legionella* spp., *Moraxella* spp., *Morganella* spp., *Neisseria* spp., *Proteus* spp., *Providencia* spp., *Salmonella* spp., *Serratia* spp., *Shigella* spp., *Staphylococcus* spp., *Stenotrophomonas* spp., *Streptococcus* spp., or *Yersinia* spp. The first epitope may be a fungal epitope, a parasite epitope or a prion epitope.

The reovirus vector may further comprise a second copy of the first epitope in the a-helical region. The second copy may be adjacent to the first epitope, or distal to the first epitope. The α-helical region may comprise a second epitope distinct from the first epitope. The second epitope may be adjacent to the first epitope, or distal to the first epitope. The second epitope may be from the same antigen as the first epitope, or different antigen as the first epitope. The second epitope may be from the same organism as the first epitope, or from a different organism as the first epitope. The second epitope may be inserted into the α-helical region of the protein, or replace one or more heptad repeats in the α-helical region of the protein.

Also provided is a reovirus particle having the features described above with respect to the vector.

In yet another embodiment, there is provided a method of inducing an immune response in a subject comprising providing to the subject a modified reovirus σ1 protein comprising a first antigenic epitope from a non-reovirus antigen located in α-helical region of the protein. The first epitope may be inserted into the α-helical region of the protein, or may replace one or more heptad repeats in the α-helical region of the protein.

The first epitope may be a viral epitope, such as from human immunodeficiency virus-1, human immunodeficiency virus-2, human T-cell leukemia virus-1, human T-cell leukemia virus-2, hepatitis B virus, human respiratory syncytial virus, influenza A virus, influenza B virus, influenza C virus, human parainfluenza virus type 1, human parainfluenza virus type 2, human parainfluenza virus type 3, human parainfluenza virus type 4a, human parainfluenza virus type 4b, mumps virus, measles virus, human metapneumovirus, Hendra virus, Nipah virus, Ebola virus, Marburg virus, SARS-associated coronavirus, herpes simplex virus-1, herpes simplex virus-2, varicella-zoster virus, Epstein-Barr virus, human cytomegalovirus, human herpesvirus-6, human herpesvirus-7, or Kaposi's sarcoma-associated herpesvirus. The first epitope may be a bacterial epitope, such as from *Acinetobacter* spp., *Aggregatibacter* spp., *Bartonella* spp., *Brucella* spp., *Burkholderia* spp., *Citrobacter* spp., *Edwardsiella* spp., *Escherichia* spp., *Haemophilus* spp., *Klebsiella* spp., *Legionella* spp., *Moraxella* spp., *Morganella* spp., *Neisseria* spp., *Proteus* spp., *Providencia* spp., *Salmonella* spp., *Serratia* spp., *Shigella* spp., *Staphylococcus* spp., *Stenotrophomonas* spp., *Streptococcus* spp., or *Yersinia* spp. The first epitope may be a fungal epitope, a parasite epitope, or a prion epitope.

The reovirus protein may further comprise a second copy of the first epitope in the a-helical region. The second copy may be adjacent to the first epitope, or distal to the first epitope. The α-helical region may comprise a second epitope distinct from the first epitope. The second epitope may be adjacent to the first epitope, or distal to the first epitope. The second epitope may be from the same antigen as the first epitope, or different antigen as the first epitope. The second epitope may be from the same organism as the first epitope, or from a different organism as the first epitope. The second epitope may be inserted into the α-helical region of the protein, or replace one or more heptad repeats in the α-helical region of the protein.

Providing may comprise administering the modified reovirus σ1 protein, such as by intramuscular, subcutaneous, nasal, oral, intravenous, transdermal, or topical administration, or by administering a vector encoding the modified reovirus σ1 protein, again by intramuscular, subcutaneous, nasal, oral, rectal, vaginal, intravenous, transdermal, or topical administration, or administering a viral particle comprising a vector encoding the modified reovirus σ1 protein, also by intramuscular, subcutaneous, nasal, oral, rectal, vaginal, intravenous, transdermal, or topical administration. The administering may be repeated, such as every week for 4 weeks, or booster treatments about every 6-12 months. The subject may be a mouse, a rabbit, a primate, or a human. The subject may be at risk of infection with or is infected by a pathogen selected from a virus, a bacterium, a parasite, a fungus, an algae, or a prion. The method may further comprise assessing an immune response to the first epitope in the subject. The immune response may be a humoral response. The method may also further comprise assessing a pathogen load following treatment. The method may also further comprise treating the subject with an antiviral, antibacterial, antifungal, or other antimicrobial agent.

In further embodiments, there are provided:
  a method of preventing or treating a bacterial infection in a subject comprising providing to the subject a modified reovirus σ1 protein comprising a first antigenic epitope from a bacterial antigen located in α-helical region of the protein;
  a method of preventing or treating a viral infection in a subject comprising providing to the subject a modified reovirus σ1 protein comprising a first antigenic epitope from a viral antigen located in α-helical region of the protein;
  a method of preventing or treating a fungal infection in a subject comprising providing to the subject a modified reovirus σ1 protein comprising a first antigenic epitope from a fungal antigen located in α-helical region of the protein;
  a method of expressing an epitope in a subject comprising providing to the subject a modified reovirus σ1 protein comprising a first antigenic epitope from an antigen located in α-helical region of the protein;
  a method of preventing or treating a parasitic infection in a subject comprising providing to the subject a modified reovirus σ1 protein comprising a first antigenic epitope from a parasite antigen located in α-helical region of the protein, such as where the epitope is selected from an amoeba, flagellate, ciliate, unicellular organism, multicellular organism, trophozoite, or cyst;

a method of preventing or treating a helminthic infection (whether in a subject comprising providing to the subject a modified reovirus σ1 protein comprising a first antigenic epitope from a helminth antigen located in α-helical region of the protein, such as where the epitope is selected from a nematode, cestode, fluke, filaria, larval form, juvenile form, adult faun, fertilized egg or unfertilized egg;

a method of preventing or treating an algal infection in a subject comprising providing to the subject a modified reovirus σ1 protein comprising a first antigenic epitope from an algal antigen located in α-helical region of the protein; or a method of preventing or treating a prion infection in a subject comprising providing to the subject a modified reovirus σ1 protein comprising a first antigenic epitope from a prion antigen located in α-helical region of the protein, such as where the epitope is selected from $PrP^C$ or $PrP^{Sc}$ of human, cow, sheep, or any other unicellular or multicellular organism.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." "About" means plus or minus 5% of the stated value.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. A schematic of the HIV-1 gp41 ectodomain. The ectodomain of gp41 is comprised of a fusion peptide (FP), N-terminal heptad repeat (NHR), C-terminal heptad repeat (CHR), and membrane-proximal external region (MPER) (Montero et al., 2008). The transmembrane region (TM) also is indicated. MPER-specific 2F5, 4E10, and Z13 mAb epitopes are displayed. Amino (N)- and carboxy (C)-terminal boundaries are shown. Numbers represent amino acid positions (SEQ ID NO:23 and 24).

FIGS. 2A-B. The structure of reovirus particles. (FIG. 2A) Virions are composed of two protein shells consisting of an outer capsid and inner core, which encloses the 10 dsRNA gene segments. Four proteins, σ1, σ3, μ1, and λ2, comprise the outer capsid. The trimeric σ1 protein is the viral attachment protein. The σ3 protein is tightly associated with μ1 and serves as a protective cap for the particle. (FIG. 2B) Cryo-EM image reconstruction of the reovirus virion with σ3 (blue), μ1 (green), and λ2 (yellow) proteins shown (Nason et al., 2001). The σ1 protein is placed schematically in the λ2 pentamers at the icosahedral vertices in the reconstruction.

(FIG. 3A) Prototype reovirus gene segment cDNA in plasmid. Cloned cDNAs representing the 10 T1L and 10 T3D dsRNA gene segments are flanked by the bacteriophage T7 RNA polymerase promoter (T7P) and the antigenomic hepatitis delta virus ribozyme (Rib). (FIG. 3B) Schematic of approach. The 10 cDNA constructs are transfected into BHK cells expressing T7 RNA polymerase (BHK-T7 cells). Nascent transcripts correspond to viral mRNAs containing the native 5' end. Self cleavage by the HDV ribozyme generates the native 3' end. Following 2 days of incubation, transfected cells are lysed by freeze-thaw, and viable virus is isolated by plaque assay using murine L929 cells. A noncoding mutation (asterisk) has been engineered into the cloned L1 cDNAs used for reverse genetics to confirm the plasmid origin of the recombinant-strain (rs) viruses.

FIG. 4. Structure of reovirus attachment protein σ1. A full-length depiction of σ1 was generated by modeling a predicted trimeric α-helical coiled coil to the N-terminus of the crystallized σ1 fragment (Reiter and Stehle, unpublished observations). The three monomers of the crystallized region are shown in red, blue, and yellow; the model is shown in grey. Tail and head regions are indicated. Amino (N)- and carboxy (C)-termini are shown. Insertion sites for the 2F5 epitope are displayed.

FIG. 5. Insertion of the 2F5 epitope into al does not alter reovirus replication in cell culture. L cells were adsorbed with the indicated viruses at an MOI of 1 PFU/cell. Titers of virus in cell lysates were determined by plaque assay at the indicated times post-infection. Results are expressed as mean viral titers for triplicate samples. Error bars indicate SD. Reovirus titers following purification from spinner-cell cultures using CsCl gradients reach ~$10^{11}$ PFU/ml (~$10^{13}$ particles/ml), depending on the cell line used.

FIG. 6. The 2F5 epitope is displayed by recombinant reovirus vectors. ELISA plates were coated with $10^{11}$ particles of either wild-type or recombinant reovirus strains containing the 2F5 epitope and incubated with 2.5 μg/ml of mAb 2F5 at 37° C. for 1 hr. Antibody binding to the 2F5 epitope on immobilized virus was detected following incubation with fluorophore-conjugated anti-human IgG. ELISA signals were quantified using a LiCor Odyssey infrared imaging system.

FIGS. 7A-C. REO-MPER vectors induce MPER-specific humoral immune responses in mice. Six-week-old, reovirus-seronegative BALB/c mice were inoculated perorally with $10^7$ PFU of (FIG. 7A) wild-type rsT1L, (FIG. 7B) rsT1L/σ1 2F5-56, or (FIG. 7C) rsT1L/σ1 2F5-154 (n=3 to 5 mice per group). Blood was collected on day 0 (pre-inoculation) and on days 14 and 70 (post-inoculation). Serial four-fold dilutions of sera starting from 1:40 were tested for (i) reovirus-specific antibodies using wells coated with rsT1L and (ii) MPER-specific antibodies using wells coated with MPER peptide (LELDKWASLWNWFDI, 2F5 epitope is underlined) by FLISA. FLISA signals were quantified using a LiCor Odyssey infrared imaging system and expressed as mean $\log_2$ reciprocal antibody titers. Error bars indicate SD. *, P<0.05 as determined by Student's t test in comparison to antibody titer on day 14.

DESCRIPTION OF ILLUSTRATIVE EMBODIMENTS

Figure 3A:
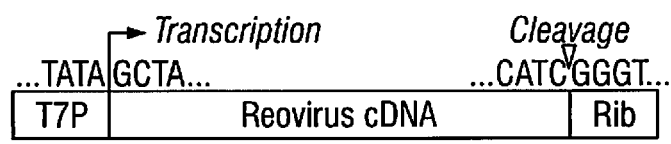
FIGS. 3A-B. Strategy to generate reovirus from cloned cDNA.

Virtually all mammals, including humans, serve as hosts for reovirus infection (Schiff et al., 2007). In humans, infection occurs via the respiratory or enteric routes and is asymptomatic in the vast majority of individuals. Disease associated with reovirus infection is rare and limited to the very young (Schiff et al., 2007). A retrospective seroprevalence study of 272 serum specimens collected from children revealed that the majority of infants are born with maternal reovirus-specific antibodies, which are lost by 6 months of age (Tai et al., 2005). Thereafter, reovirus seroprevalence steadily increases by about 10% per year, at least until the age of 5 years when the study was terminated (Tai et al., 2005). In case reports of children with reovirus disease, all have been less than three months of age and all recovered from infection without sequelae (Giordano et al., 2002; Hermann et al., 2004; Tyler et al., 2004).

Following peroral inoculation of mice, the preferred experimental model for studies of reovirus pathogenesis and immunity, reovirus initiates infection by transcytosis across M cells overlying Peyer's patches (PPs) in the small intestine (Wolf et al., 1981; Fleeton et al., 2004). In mouse ileal-loop studies, reovirus virions are visualized by electron microscopy on the surface of M cells, inside vesicles within M cells, and in the intercellular pocket between the basolateral surface of intestinal epithelial cells and mononuclear cells (Wolf et al., 1981; Organ and Rubin, 1998). After M cell transcytosis, reovirus initiates infection at the basolateral surface of adjacent epithelial cells and mononuclear cells in the PP. Virus subsequently disseminates to the mesenteric lymph nodes and spleen (Fleeton et al., 2004; Johansson et al., 2007; Antar et al., 2009).

Reovirus induces both humoral and cell-mediated immune responses within gut-associated lymphoid tissue (GALT). The humoral immune response following peroral inoculation of mice with strain T1L is characterized by mucosal IgA production through priming of B lymphocytes and development of plasma cells in PPs, mesenteric lymph nodes, and spleen (London et al., 1987). IgA responses are directed against reovirus structural proteins σ1, σ3, and μ1 (London et al., 1987). Serum IgG of mainly the IgG2a, IgG2b, and less frequently IgG1 subclasses also is produced following peroral inoculation. IgG responses are directed against reovirus structural proteins, σ1, σ3, μ1, and λ2 (Major and Cuff, 1996; Virgin et al., 1991; Tyler et al., 1993). Reovirus-specific IgA and IgG antibodies in mice prevent viral intestinal infection and systemic dissemination (Major and Cuff, 1996), respectively.

Despite the attractiveness of the reovirus system, the ability to exploit these positive features remains limited. Reasons for these limitations include complicated issues of heterologous antigen folding, antigen presentation and antigen context. The present inventors hypothesize that the σ1 and σ3 proteins of reovirus can be modified to carry α-helical epitopes of pathogens in the proper structure and context to both (a) be recognized by a host immune system as foreign, and (b) generate a protective immune response.

Human neutralizing antibodies targeting the gp41 MPER have been shown to recognize reoviruses engineered to display MPER sequences within surface-exposed regions of reovirus capsid proteins σ1 that form α-helices. Thus, the isolated MPER can apparently mimic the native MPER conformation in the context of α. MPER-expressing reoviruses will be tested for replication efficiency, stability during serial passage in cell culture, and retention of native MPER-specific epitopes. These MPER-expressing reoviruses will next be tested for their ability to generate a protective immune response in MPER naïve animals. Finally, the recombinant reovirus vectors inducing the most potent HIV-1-specific humoral immune responses will be tested for their ability to protect non-human primates against HIV challenge. These and other aspects of the invention will be discussed in detail below.

I. Reoviridae

Beginning in 1959, viruses that were typically isolated from the respiratory and gastrointestinal tracts and not associated with any known disease state were classified as reovirus (respiratory enteric orphan viruses) (Sabin, 1959). During the 1970s, the family enlarged and currently constitutes twelve genera. The general characteristics of the Reoviridae family are non-enveloped virus particles between 60 and 85 nm in diameter. Virions are comprised of a double protein capsid shell with icosahedral symmetry containing a genome comprised of 10-12 segments of dsRNA (see FIGS. 2A-B). Of the 12 genera, four—Orthoreovirus, Rotavirus, Coltivirus, and Seadornavirus—infect humans. These viruses have similar structural features and replication strategies.

Reoviruses are resistant to solvents, quaternary ammonium salts, phenol, alcohol, pH and heat (50° C. for 1 hr). These viruses survive pasteurization and the most common human strains are also the most common bovine strains. Although reoviruses are not known to be associated with any particular disease, most people have been exposed to these agents by the time they reach early adulthood (Jackson & Muldoon, 1973; Stanley, 1974; Tai, 2005).

Reoviruses attach to host cells via the filamentous attachment protein, al (Furlong et al., 1988; Fraser et al., 1990). The σ1 protein of all three reovirus serotypes engages junctional adhesion molecule-A (JAM-A) (Barton et al., 2001b; Campbell et al., 2005), an integral component of intercellular tight junctions (Martin-Padura et al., 1998; Liu et al., 2000). Following attachment to cell-surface receptors, reovirus internalization is mediated by β1 integrins (Maginnis et al., 2006), most likely via clathrin-dependent endocytosis (Ehrlich et al., 2004). In the endocytic compartment of most cell types, reovirus outer-capsid protein σ3 is removed by acid-dependent cysteine proteases in most cell types (Baer and Dermody, 1997; Ebert et al., 2002). Removal of σ3 results in the exposure of a hydrophobic conformer of the viral membrane-penetration protein, μ1, which pierces the endosomal membrane allowing delivery of transcriptionally active reovirus core particles into the cytoplasm (Chandran et al., 2002; Odegard et al., 2004) where the remainder of the replication cycle is completed.

The normal mode of viral transmission for reovirus depends on the virus surviving the environment and passage through the gut to find a few permissive rapidly dividing cells in the intestine. In these cells, the virus replicates to a lytic endpoint. With so few cells involved, symptoms do not result. The viruses are shed into the environment to complete the cycle (Neutra, 1999). It is important to note that the virus has no latent state—if the virus is not blocked intracellularly, replication progresses invariably to cell lysis—the mechanism of viral release.

A. Reovirus

Of particular interest to the present invention is the use of an Orthoreovirus. It is well known to those of skill in the art that the common name for the family Reoviridae and for the specific genus Orthoreovirus is simply reovirus. Thus, in the present invention, the term "reovirus" is all inclusive of the genus Orthoreovirus and all of the viruses contained within this genus, for example, but not limited to mammalian reovirus, avian reovirus, and Nelson Bay virus.

In this genus, the virions measure 60-85 nm in diameter and possess two concentric capsid shells, each with icosahedral symmetry. The genome consists of double-stranded RNA in 10 discrete segments, with a total genome size of approximately 24 kbp encoding 11-12 translated proteins.

Mammalian reoviruses are ubiquitous agents that infect a variety of mammalian species. Although mammalian reoviruses share a common group antigen, three serotypes were identified by neutralization and hemagglutination-inhibition tests. These serotypes were isolated from humans and are as follows: type 1 (prototype strain Lang), type 2 (prototype strain Jones) and type 3 (prototype strains Dearing and Abney) (Sabin, 1959; Fields, 1996).

B. Other Reoviridae Viruses

It is also contemplated that the species in the genus Rotavirus may be used in the present invention. It is well known that rotaviruses and reoviruses share common structural features. Thus, it is within the scope of the present invention that rotaviruses may also be generated using the techniques described herein.

Yet further, the scope of the present invention is not limited to the genera Orthoreovirus and Rotavirus, and includes the use of other viruses that are classified as a Reoviridae virus and have similar structural features as reovirus.

C. Reoviridae Infectivity of Cells

Mammalian reoviruses recognize sialic acid (Armstrong et al., 1984; Gentsch & Pacitti, 1985; Paul et al., 1989) and junctional adhesion molecule-A (JAM-A) on the surface of host cells. (Barton et al., 2001b; Campbell et al., 2005) Reovirus binds efficiently to a multitude of cell lines and as such can potentially target many different tissues.

II. Producing Modified Reoviruses

A. Reovirus Reverse Genetics

As discussed above, mammalian orthoreoviruses (reoviruses) are members of the Reoviridae family and have been studied extensively (Barton et al., 2001a; Ebert et al., 2002; Ehrlich et al., 2004; Connolly et al., 2000; O'Donnell et al., 2005; 2006). The inventors previously reported the development of an entirely plasmid-based reverse genetics system for mammalian reoviruses in which viable viruses are generated from cloned cDNAs. See U.S. Ser. No. 11/960,357, incorporated herein by reference. Neither helper virus nor coexpression of viral replication proteins is required for recovery of wild-type (wt) virus or engineered viral mutants. The establishment of plasmid-based reverse genetics for reovirus allows exploration of reoviruses as modalities to elicit protective immunity against a variety of pathogens.

Figure 3B:
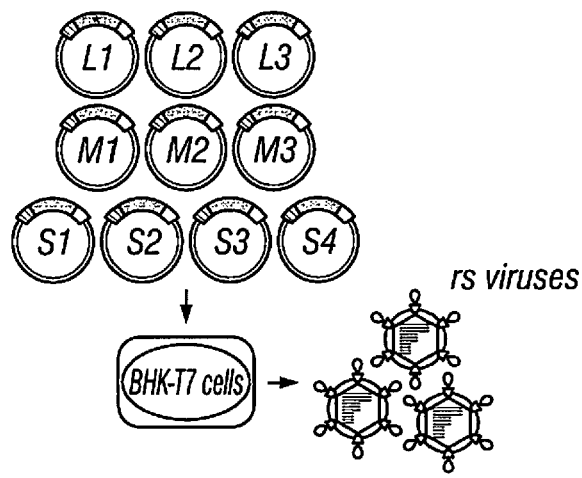

The system permits selective introduction of desired mutations into cloned cDNAs encoding each of the 10-12 viral gene segments, followed by isolation of mutant viruses from cells transfected with the plasmid constructs. See FIGS. 3A-B. Importantly, recombinant viruses are generated without a requirement for helper virus and free of any selection. Thus, this new technique provides a means to directly and precisely engineer the viral genome in the context of infectious virus. For example, this system was used to engineer mutations in the σ1, σ3, and μ1 proteins. These proteins form part of the viral outer capsid, which is responsible for numerous major events in reovirus interaction with the cell and host, including attachment, disassembly within endosomes, penetration of cell membranes, induction of apoptosis, growth in the intestine and dissemination from that site, pathways of spread, neurovirulence, and tropism within the CNS (for reviews, see Chandran and Nibert, 2003; O'Donnell et al., 2003; Guglielmi et al., 2006).

B. Modification of Reovirus Proteins

Figures 4, 5, 6:
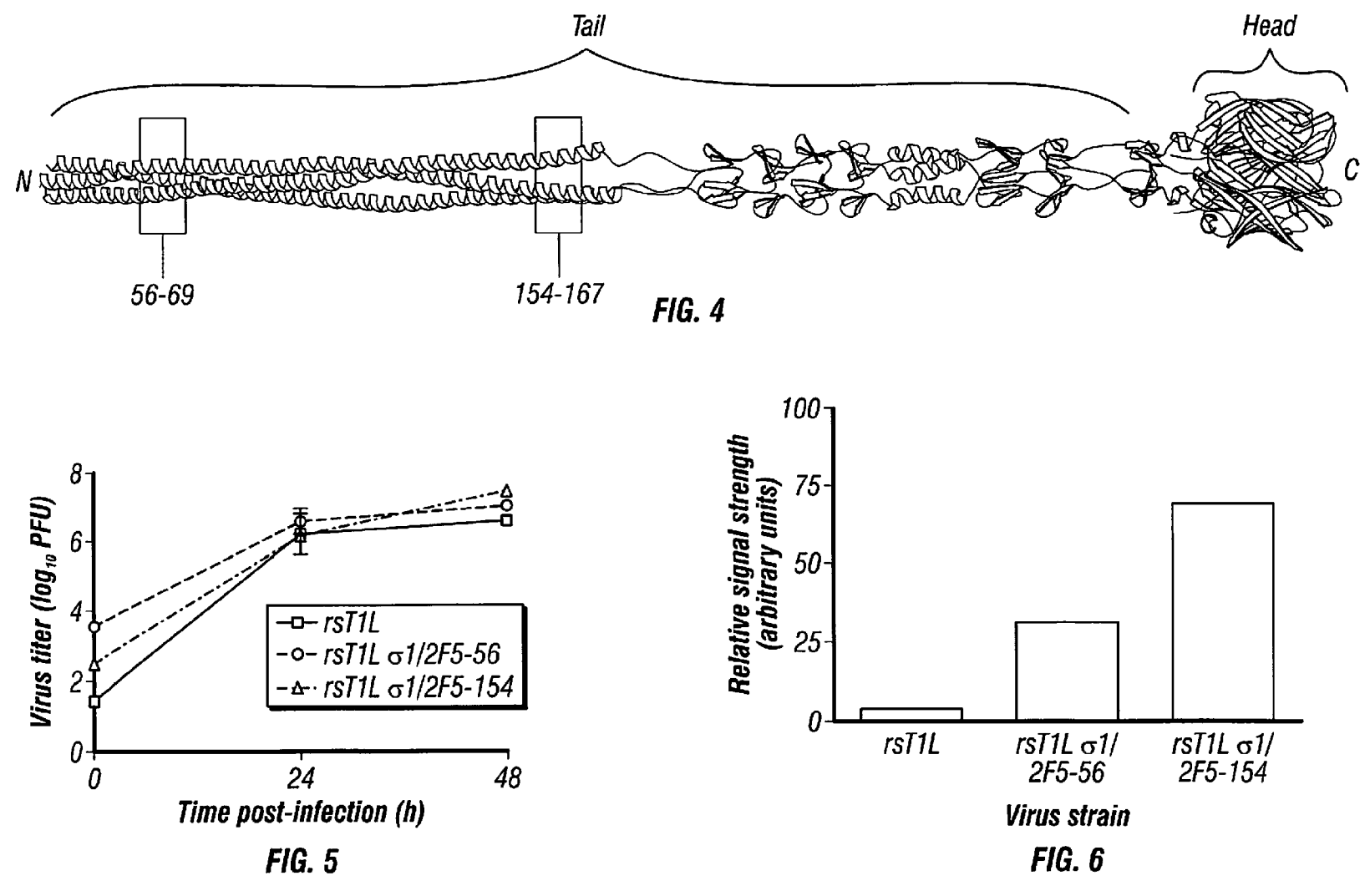
Figure 8:
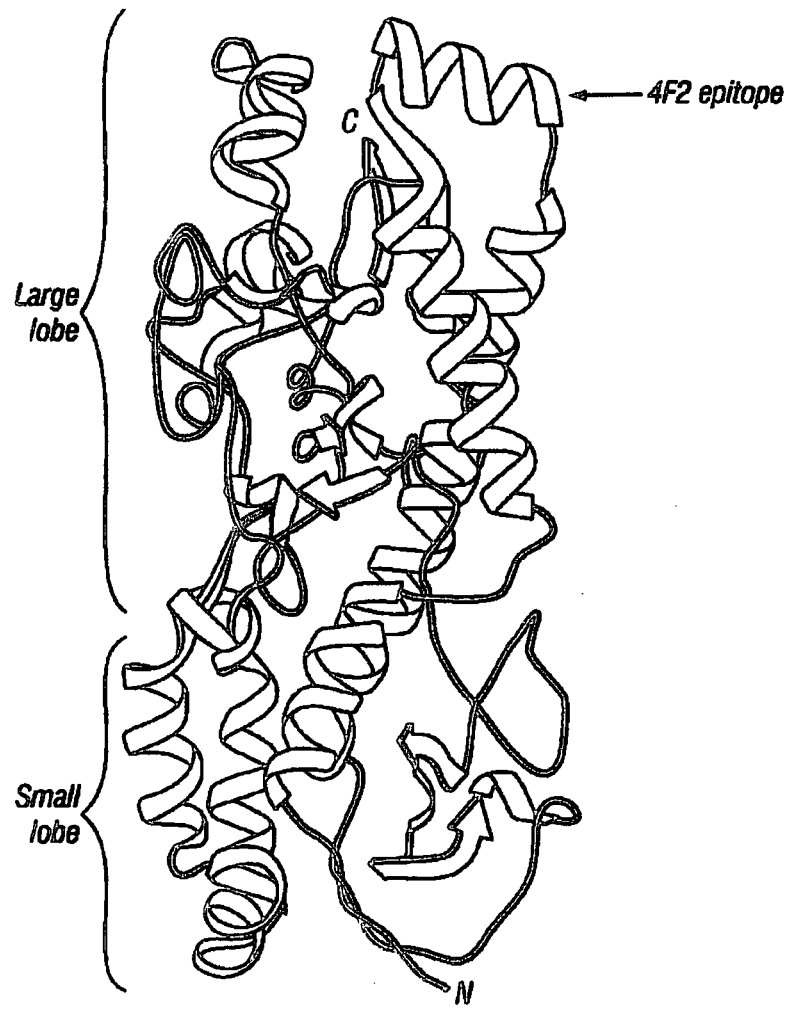
FIG. 8. Structure of reovirus outer-capsid protein σ3. The σ3 protein contains two major lobes, a virion-proximal small lobe and a virion-distal large lobe that is solvent exposed (Olland et al., 2001). Amino (N)- and carboxy (C)-termini are indicated. The σ3 α-helix targeted for replacement with MPER sequences corresponds to the σ3-specific mAb 4F2 epitope and is shown in red.

Of particular interest with respect to the present invention are the σ proteins of reovirus, including σ1 and σ3. Reovirus attachment protein σ1 has a modular organization with three tandemly arranged structural regions: an N-terminal α-helical coiled coil (residues 1 to ~170), a triple β-spiral interrupted by a short region of α-helix (residues ~170 to 309), and a C-terminal globular region (residues 310 to 455) (Chappell et al., 2002; Nibert et al., 1990) (FIG. 4). Collectively, residues 1-309 comprise the σ1 tail, and residues 310-455 form the σ1 head. The inventors propose that α-helical coiled-coil sequences derived from other pathogens can be inserted into structurally homologous regions of the σ1 tail and retain native immunogenicity. The structure of σ3, which also includes an α-helical region, is shown in FIG. 8.

There are several different options for inserting of α-helical epitopes. A first option is simply to replace one of the heptad repeats with the epitope of interest. A second option is to insert two copies of the epitope by replacing two heptad repeats, either adjacent to each other, or separated by 1, 2, 3, 4, 5, 6, 7, 8, 9, 10 or more intact repeats. A third option is to insert an epitope of interest, or multiple copies (either adjacent or not) into the σ1 or σ3 α-helical region. A fourth option is to insert an epitope of interest, or multiple copies (either adjacent or not) into the σ1 protein in combination with an epitope inserted into the σ3 protein.

In other embodiments, the insertions into or replacements within the heptad repeats may be more or less random. It is also contemplated that additional sequences may be appended to the N- or C-termini of the inserted epitopes to enhance spacing and alpha helical conformation. In general, the total size of the insert will be roughly no larger than the portion of fragment of the σ protein replaced.

C. Transformation

In certain embodiment, the present invention will employ gene transfer techniques to build the recombinant reoviruses of the present invention. Suitable methods for delivery to cells of a reovirus genome or fragments thereof into a cell are known to one of ordinary skill in the art. Such methods include, but are not limited to, direct delivery of DNA such as by ex vivo transfection (Wilson et al., 1989; Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome-mediated transfection/lipofection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985); and any combination of such methods. Through the application of techniques such as these, organelle(s), cell(s), tissue(s) or organism(s) may be stably or transiently transformed.

D. Culturing

Cultured cell lines vary to a great extent in their ability to support reovirus production. In U.S. Pat. No. 6,703,232, a variety of cells were employed and HEK 293 cells proved to be very efficient at producing reovirus. HEK 293, Vero and L929 cells were grown to confluence and infected with reovirus at a multiplicity of infection (MOI) of 1 plaque-forming unit (PFU)/cell. The yield of virus was determined at various time post infection. HEK 293 cells, which previously had not been reported to support reovirus growth, produced almost 50 times more reovirus at 24 hours post-infection than L929 cells, which are routinely used to culture mammalian reovirus. Vero cells produced less reovirus at this point, yielding 3000 times less reovirus than the HEK 293 cells.

At 36-48 hours post-infection, the virus yield in the HEK 293 cells began to plateau, but the titer was still one order of magnitude higher than the titer produced in L929 cells, and two orders of magnitude higher than that of Vero cells. It was not until 96 hours post-infection that all three cells lines produced about the same titer of reovirus, at $10^9$ to $10^{10}$ per milliliter. These results indicate that the HEK 293 cell is a very efficient system for the production of reovirus, allowing for shortened production time which will markedly reduce the cost of production.

To further optimize the HEK 293 cell production conditions, reovirus was used to infect the HEK 293 cells at various MOI, and the yield was determined. The results suggest that a lower m.o.i. was even more advantageous. Thus, at 48 hours post-infection, the cells which were inoculated at a MOI of 0.5 PFU/cell produced more than $10^{10}$ viruses per ml, which was the maximal yield at these culture conditions. After this point, the titer went down by about two-fold, and reached the maximal yield again at 96 hours. A similar pattern was observed for the culture with an initial MOI of 0.1/cell. Consequently, the best time to harvest reovirus under these culture conditions appears to be 36-60 hours post infection. At this period of time, the titer is high, and the virus is still associated with the cell fragments and membranes, which makes purification of the virus relatively simple. At 96 hours, all the cells have lysed and the virus is released into the media along with the degradation products of the dead cells, making purification much more complicated than when the virus is cell associated.

For best efficiency, the virus should be harvested when the yield is sufficiently high but most of the virus is still associated with the cells. The harvest time should be determined empirically when culture conditions are varied. To determine if the virus is associated with the cells, a small aliquot of the culture can be examined, e.g., under microscopy, to determine the degree of cell viability at different time points after infection. Alternatively, vital staining can be conducted to determine the percentage of viable cells. To simplify the purification process, the virus is typically harvested before all the cells have been lysed. In particular, the virus is harvested when 20-95% of the cells remain viable. Even more particularly, the virus is harvested when 35-90%, and most particularly 50-80%, of the cells remain viable.

HEK 293 cells are adherent cells that can be grown in cell culture flasks, roller bottles, microcarrier systems or hollow fiber systems, or any other system that is suitable for growing adherent cells. HEK 293 cells may be modified to generate derivative cells. For example, the 293/SF cell (ATCC Number CRL-1573.1) was derived from the HEK 293 cell and adapted to serum-free culture conditions. The 293/SF cells grow as a mixture of adherent and suspension cells and may be grown in any of the culture containers described above, as well as spinner bottles, stirred vessels (fermenters), hollow fiber systems, or any other culture containers suitable for suspension cells.

In order to produce industrial amounts of reovirus, 293/SF cells can be cultured in 15 L spinner flasks and infected with reovirus at a MOI of 0.5 PFU/cell when cell density reaches $10^6$ cells/ml. The culture is incubated until cell lysis begins, as evidenced by the culture media color change from red to orange due to the presence of Phenol Red in the media, or by a viable cell count under the microscope. At this point, the virus may be harvested by centrifugation. The virus can then purified as described below. For storage, the virus can be frozen or lyophilized according to methods established in the art, with or without stabilizing agents.

E. Purification of Virus

It may be desirable to purify the Reoviridae virus, modified virus or variants thereof. Purification techniques are well known to those of skill in the art. Analytical methods particularly suited to the preparation of a pure viral batch are tangential flow concentration or cesium chloride ultra-centrifugation (January, 1971).

Certain aspects of the present invention concern the purification, and in particular embodiments, the substantial purification, of the modified virus. The term "purified modified virus" as used herein, is intended to refer to a virus or viral batch or viral stock that is purified to any degree relative to its naturally-obtainable state.

Generally, "purified" will refer to a virus or viral batch or stock that has been subjected to fractionation to remove various other components and which composition substantially retains its expressed biological activity. Where the term "substantially purified" is used, this designation will refer to a composition in which the virus or viral batch or viral stock forms the major component of the composition, such as constituting about 70%, 80%, 90%, 95% or 99% or more of the virus or viral batch or viral stock in the composition.

Yet further, the virus can be purified by affinity purification with elution at low pH. The virus is then concentrated by saturated ammonium sulfate and dialyzed by tangential flow to remove small molecules.

Various methods for quantifying the degree of purification of the virus or viral batch or viral stock will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the virus or viral batch or viral stock exhibits a detectable activity. In specific embodiments, the tissue infective dose (TID) per unit protein of the crude cell lysate is calculated and compared to the TID/protein ratio of the purified viral fraction and to the TID/protein ratio following cesium chloride gradient purification.

IV. Epitopes

As discussed, the present invention may be applied with any of a wide variety of different antigens. The following organisms are considered suitable targets for generation of immune responses as described herein.

A. Viral Epitopes

Virus targets include human immunodeficiency virus-1, human immunodeficiency virus-2, human T-cell leukemia virus-1, human T-cell leukemia virus-2, hepatitis B virus, human respiratory syncytial virus, influenza A virus, influenza B virus, influenza C virus, human parainfluenza virus type 1, human parainfluenza virus type 2, human parainfluenza virus type 3, human parainfluenza virus type 4a, human parainfluenza virus type 4b, mumps virus, measles virus, human metapneumovirus, Hendra virus, Nipah virus, Ebola virus, Marburg virus, SARS-associated coronavirus, herpes simplex virus-1, herpes simplex virus-2, varicella-zoster virus, Epstein-Barr virus, human cytomegalovirus, human herpesvirus-6, and human herpesvirus-7, Kaposi's sarcoma-associated herpesvirus.

B. Bacterial Epitopes

Bacterial targets include *Acinetobacter* spp., *Aggregatibacter* spp., *Bartonella* spp., *Brucella* spp., *Burkholderia* spp., *Citrobacter* spp., *Edwardsiella* spp., *Escherichia* spp., *Haemophilus* spp., *Klebsiella* spp., *Legionella* spp., *Moraxella* spp., *Morganella* spp., *Neisseria* spp., *Proteus* spp., *Providencia* spp., *Salmonella* spp., *Serratia* spp., *Shigella* spp., *Staphylococcus* spp., *Stenotrophomonas* spp., *Streptococcus* spp., and *Yersinia* spp.

C. Fungal Epitopes

Fungal targets include cell wall, capsular, intracellular, and secreted components of yeasts, molds, and dimorphic fungi to include, but not limited to, Cryptococcus, Mucor, Rhizopus, Pseudallescheria, Histoplasma, Blastomyces, Trichophyton, Microsporum, Candida, Aspergillus, Blastomyces, Coccidioides, Paracoccidioides, Epidermophyton, Paracoccidioides, Sporothrix, Trichosporon, and Fusarium.

D. Parasite Epitopes

Parasitic pathogens include protozoa, trypanosomes, tapeworms, roundworms, and helminths.

E. Polytopes

In certain embodiment, it may be desirable to include multiple distinct epitopes into a single reovirus σ protein. The epitopes may be distinct epitopes from the same antigen, from different antigens of the same pathogens, or even from different pathogens. Examples include use of epitopes from a variety of antigenically distinct strains of a single type of virus or bacterium, or epitopes from a group of taxonomically distinct viruses or pathogens that are prevalent in a particular geographic location.

F. Exemplary Epitopes

The following table sets forth exemplary but non-limiting examples of epitopes for use in accordance with the present invention.

TABLE 1

| Virus | Viral Protein | Sequence | References |
|---|---|---|---|
| Human immunodeficiency virus (HIV) | gp160 | 656-NEQELLELDKWASL-669 (SEQ ID NO: 1)<br>672-WFDITNWL-679 (SEQ ID NO: 2) | (Muster et al., 1993; Zwick et al., 2001a; Zwick et al., 2001b) |
| Human T-cell Lymphotropic virus type 1 (HTLV-1) | gp21 | 48-SMSLASGKSLLHEVDKDISQLTQAIVKHNKNLLK IAQYAAQNRRGLDLLWEQGGL-103 (SEQ ID NO: 3) | (Kobe et al., 1999) |
| Human T-cell Lymphotropic virus type 1 (HTLV-2) | gp21 | 41-SLASSKSLLFEVDKDISHLTQAIVKNHQNILRVA QYAAQNRRGLDLLFWEQGGL-104 (SEQ ID NO: 4) | (Eiraku et al., 1996) |
| Ebola virus | Gp | 551-QDGLICGLRQLANETTQALQLFLRATTELRTFSI LNRKAIDFLLQRW-597 (SEQ ID NO: 5) | (Weissenhorn et al., 1998a; Weissenhorn et al., 1998b) |
| Marburg virus | Gp | 551-QNNLVCRLRRLANQTAKSLELLFRVTTEERTFSL INRHAIDFLLQRW-597 (SEQ ID NO: 6) | (Weissenhorn et al., 1998b) |
| Respiratory syncytial virus (RSV) | F | 145-GSIASGIAVSKVLHLEGEVNKIKNALLSTNKAVV SLSNGVSVLTSKVLDLKNYINNRL-202 (SEQ ID NO: 7)<br>483-GSSDEFDASISQVNEKINQSLAFIRRSDELLHNVNTGKS TTNY-525 (SEQ ID NO: 8)<br>58-GSELSNIKETKCNGTDTKVKLIKQELDKYKNAVTELQLLMQ NT-100 (SEQ ID NO: 9) | (Matthews et al., 2000) |
| Human metapneumovirus (hMPV) | F | HR1-LESEVTAIKNALKKTNEAVSTLGNGVRVLATAVRELKDFVSKN (SEQ ID NO: 10)<br>HR2-KFPEDQFNVALDQVFESIENSQALVDQSNRILSSAEK (SEQ ID NO: 11) | (Miller et al., 2007) |

TABLE 1 -continued

| Virus | Viral Protein | Sequence | References |
|---|---|---|---|
| Nipah virus | F | HR1-AMKNADNINKLKSSIESTNEAVVKLQETAEKTVYVLTALQDY (SEQ ID NO: 12)<br>HR2-KVDISSQISSMNQSLQQSKDYIKEAQRLLDTVN (SEQ ID NO: 13) | (Xu et al., 2004) |
| Hendra virus | F | HR1-AMKNADNINKLKSSIESTNEAVVKLQETAEKTVYVLTALQDY (SEQ ID NO: 12)<br>HR2-KVDISSQISSMNQSLQQSKDYIKEAQKILDTVN (SEQ ID NO: 14 | (Xu et al., 2004) |
| Measles virus | F | 103-FAGVVLAGAALGVATAAQITAGIALHQSMLNSQAIDNLRASLET TNQAIEAIRQAGQEMILAVQGVQDYINNELIPSMNQLSC-185 (SEQ ID NO: 15)<br>426-PDAVYLHRTDLGPPISLERLDVGINLGNAIAKLEDAKELLESSDQILR SM-477 (SEQ ID NO: 16) | (Baker et al., 1999) |
| Mumps virus | F | 103-FAGIAIGIAALGVATAAQVTAAVSLVQAQTNARAIAAMKNSIQATN RAVFEVKEGTQQLAIAVQAIQDHINTIMNTQLNNMSC-185 (SEQ ID NO: 17)<br>426-SNITYAENLTISLSQTINTQPIDISTELSKVNASLQNAVKYIKESNHQ LQSV-477 (SEQ ID NO: 18) | (Baker et al., 1999) |
| Severe acute respiratory syndrome (SARS) coronavirus | Spike | 879-PFAMQMAYRFNGIGVTQNVLYENQKQIANQFNKAISQIQESLTTTSTAL GKLQDVVNQNAQALNTLVKQLSSNFGAISSVLNDILSRLDKVEAEVQIDRLIT GRLQSLQTYVTQQLTRAAEIRASANLAATKM-1011 (SEQ ID NO: 19)<br>1125-PELDSFKEELDKYFKNHTSPDVDLGDISGINASVVNIQKEIDRLNEVA KNLNESLIDLQELGKYEQYIK-1193 (SEQ ID NO: 20) | Bosch et al., 2004. Tripet et al., 2004) |
| Influenza A virus | HA | 38-LKSTQAAIDQINGKLNRVIEKTNEKFHQIEKEFSEVEGRIQDLEKYVEDTK IDLWSYNAELLVALEN-114 (SEQ ID NO: 21) | (Bullough et al., 1994) |

V. Treatments

A. Pharmaceutical Formulations

Where clinical applications are contemplated, it will be necessary to prepare the reovirus compositions of the present invention in a form appropriate for the intended application. Generally, this will entail preparing compositions that are essentially free of pyrogens, as well as other impurities that could be harmful to humans or animals.

One will generally desire to employ appropriate salts and buffers to render agents stable and allow for suitable administration. Aqueous compositions of the present invention comprise an effective amount of the reovirus particles, dissolved or dispersed in a pharmaceutically acceptable carrier or aqueous medium. Such compositions also are referred to as inocula. The phrases "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the reovirus particles of the present invention, its use in therapeutic compositions is contemplated. Supplementary active ingredients also can be incorporated into the compositions.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, particular methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration, the reovirus particles of the present invention should be formulated such that they are stable under a variety of environmental conditions. A variety of stabilization methods have been used, including:
- a) Low temperatures (−10° C. to −70° C.). Most vaccines are stable during storage at extremely low temperatures. However, low temperature storage facilities are costly and are not always available; this limits the utility and practicality of this approach.
- b) Lyophilization. Freeze-dried vaccines are reasonably stable and can be stored at 2-8° C. for a predefined length of time. Lyophilization may, however, result in a loss of viral titer during drying thereby reducing the yield of the manufacturing process. In addition, during long-term storage, a lyophilized vaccine may still deteriorate, to the point where it may or does not have sufficient titer to confer immunization. Furthermore, since a lyophilized vaccine requires reconstitution prior to use, a liquid reconstituted preparation may lose potency while standing at room temperature before use. This loss of titer during reconstitution may also result in insufficient titer to confer immunity.
- c) Stabilizers. These are specific chemical compounds that interact and stabilize biological molecules and/or general pharmaceutical excipients that are added to the vaccine and are used in conjunction with either lower temperature storage or lyophilization methods.

These oral formulations can be prepared by either (1) dilution of bulk vaccine into the stabilizer, (2) dialysis/diafiltration into the stabilizer, or (3) concentration of bulk vaccine and diafiltration into the stabilizer, followed by lyophilization if required.

The amounts and concentrations of the components of the oral formulations described herein will be understood by those skilled in the art to refer to the gram/100 milliliters percentage when referring to lyophilized or liquid formulations. For example, a 10% concentration in a liquid formulation is 10 grams per 100 milliliters and a 10% concentration of a lyophilized formulation refers to 10 grams per 100 milliliters after reconstitution of the lyophilized formulation with an appropriate diluent. Other measures, such as the molarity of a compound, refer to a liquid formulation or to a lyophilized oral formulation after reconstitution with an appropriate diluent.

The stabilizer composition of the present invention may contain the following ingredients in about the amounts indicated. For convenience the amounts are stated round numbers. However, one skilled in the art will recognize that amounts within 10 or 20 percent of the stated values can also be expected to be appropriate, i.e., where 20% is stated, a range of from 16-18% to 22-24% is implicit and can be appropriate:

Sucrose: 1-70% (w/v)
Sodium or potassium phosphate: 0.01-2 M
Sodium succinate or sodium citrate: 0.05-2 M
Tissue culture medium, saline, or water: 0-balance of remaining volume For lyophilized oral formulations:
Sodium phosphate 0.05-2 M
Sucrose 1-20% (w/v)
Mannitol 1-20% (w/v)
Lactose 1-20% (w/v)
In addition, the following can also be present:
Hydrolyzed gelatin 2.5% (w/v)
Sodium chloride 150 mM
Sodium glutamate 7 mM.

The following compounds can be used in place of sucrose, and at comparable osmolality: fucose, trehalose, polyaspartic acid, inositol hexaphosphate (phytic acid), sialic acid or N-acetylneuraminic acid-lactose. Also, any suitable sugar or sugar alcohol such as dextrose, mannitol, lactose, or sorbitol, can be substituted for sucrose at concentrations effective in achieving the desired stabilization. The concentration of sugar relates to the viscosity of the formulation. In instances where reduced viscosity is desired, it is known in the art to be preferable to use lower concentrations of sugar, e.g., sucrose. It will also be appreciated by persons in the art that the upper limit for the concentration of sugar can be dictated by the ability of a formulation to undergo required filtration or processing steps.

Another sugar compound that can be used to stabilize liquid oral embodiments of the vaccine formulations taught herein is polysorbate, a chain of multiple sorbose units. Liquid oral formulations are made as taught herein with the addition of polysorbate. Polysorbate can be obtained in a variety of chain lengths from. It is preferred that when adding polysorbate, a chain length between 20 and 80 units is employed. A concentration of about 0.01% to about 0.50% polysorbate 80 or polysorbate 20 in a liquid formulation is most preferred.

Amino acids can be employed in the lyophilized oral formulations taught herein. It has been found that some amino acids, particularly charged amino acids can improve the stability of a vaccine prepared in the lyophilized oral formulations. Preferred amino acids are arginine, glutamate and glutamine. A concentration of about 0.5% to about 2% dry weight is appropriate. A concentration of about 0.75% to about 1.25% dry weight is preferred and a concentration of about 1% dry weight is most preferred in lyophilized formulations. A combination of amino acids can be used but the overall concentration of the combined amino acids should be no more than 2.0%.

Another excipient useful in both liquid and lyophilized oral formulations of vaccines as taught herein is recombinant human albumin. Recombinant human serum albumin is produced using gene expression systems and therefore is safer to use than albumin isolated from the serum of human beings. The concentration of the albumin is typically in the range of about 0.1 to about 2%, particularly about 1.0%.

Tissue culture medium, saline or water can be used as a diluent. Frequently, Williams' E medium ("WE") is used, i.e., either Williams' E medium or Williams' medium E modified.

Also, buffering agents to neutralize gastric acid are not limited to citrate, phosphate and succinate and could include bicarbonate or common carboxylic acids (carboxylates) such as, but not limited to, fumarate, tartrate, lactate, maleate, etc. The appropriateness of any of these can be assessed by simply trying a formulation in which these agents are substituted or combined with phosphate, citrate or succinate. Up to about 2.0 M carboxylates can be used in the liquid and lyophilized formulations of this invention, however, the inventors prefer to use less than about 1.0 M, e.g., about 0.05-0.9 M, and can be less than about 0.7 M, e.g., 0.05 to about 0.7 M. It is also contemplated to use less than 0.5 M, e.g., about 0.05 to 0.45 M. Particular concentrations in these ranges can be appropriate. Also, higher concentrations of buffering components (e.g., phosphate, succinate, citrate) can be used if, for example, additional gastric neutralization is required. In instances where additional buffering capacity is useful in phosphate/citrate or phosphate/succinate buffers, it is contemplated to further increase the concentrations of succinate or citrate as the buffering agent rather than phosphates.

Up to about 2.0 M phosphate can be used in the liquid and lyophilized oral formulations of this invention, however, once can use less than about 1.0 M, e.g., about 0.010-0.8 M, and often less than 0.5 M, e.g., about 0.010 to 0.45 M. It is most contemplated to use less than about 0.35 M, e.g., 0.010-0.30M. Particular concentrations in these ranges can be appropriate. In liquid oral formulations, one can maintain the concentration of phosphate about or below 0.30 M, e.g., 0.010-0.35 M to avoid the precipitation of phosphate salts, e.g., during long-term storage or freeze/thaw cycles. Thus, the upper limit for the concentration of phosphate in any particular formulation can be dictated by the formation or precipitation of phosphate salts and whether the salts negatively affect the performance of the oral formulation in areas such as stability and administration. Particular concentrations can be readily determined for any particular formulation by standard empirical testing including pH adjustments in the range of pH 6-8.

Oral formulations may also be used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Routes of Administration and Dosing Regimens

Administration of the pharmaceutical compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

C. Therapeutic Adjuncts

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GM-CSF, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or down-regulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as λ-interferon, IL-2, or IL-12 or genes encoding proteins involved in immune helper functions, such as B-7.

VI. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Results

As a proof-of-principle that α-helical regions from heterologous viruses can be grafted into the a1 protein, the inventors substituted two heptad repeats from the HIV-1 gp41 MPER for two heptad repeats in σ1 (FIG. 4). The MPER sequences chosen for insertion incorporate the 2F5 epitope, which elicits broadly neutralizing antibody responses against HIV-1 (Zwick et al., 2001; Parker et al., 2001; Shen et al., 2009). Nucleotides encoding amino acids 56 to 69 or 154 to 167 of σ1 from strain T1L were replaced with sequences encoding residues 656 to 669 of HIV-1 gp160 (the precursor of gp41) from HIV-1 strain Ba-L (656-NEQELLELDK-WASL-669 (SEQ ID NO:1)) in an S1 gene plasmid vector. This region encompasses the entire 2F5 core epitope (662-ELDKWASL-669 (SEQ ID NO:22)). The resulting plasmids were used to generate recombinant-strain (rs) reoviruses by reverse genetics (Kobayashi et al., 2007; Kobayashi et al., 2010). MPER-expressing rs reoviruses and wild-type rsT1L as a control were isolated from cell lysates by plaque purification using murine L929 (L) cells and purified using CsCl gradients. Insertion of the 2F5-encoding sequence into the viral genome was confirmed by nucleotide sequence analysis of viral dsRNA. Thus, sequences in HIV-1 that elicit neutralizing antibodies can be introduced into reovirus attachment protein σ1.

To determine whether insertion of MPER sequences into the σ1 protein alters reovirus replication in cell culture, the inventors quantified viral titers following infection of L cells at a multiplicity of infection (MOI) of 1 PFU/cell (FIG. 5). Replication kinetics of MPER-expressing recombinant reoviruses were indistinguishable from those of wild-type rsT1L, with all viruses reaching comparable titers at 24 h and 48 h post-infection. These data indicate that substitution of α-helical regions of σ1 with a structurally homologous region of HIV-1 gp41 does not alter reovirus replication.

To determine whether the 2F5 epitope is exposed on the surface of recombinant reovirus particles, the inventors used an enzyme-linked immunosorbent assay (ELISA) to detect the binding of 2F5 mAb to immobilized purified reovirus virions (FIG. 6). In these experiments, 2F5 mAb bound to viruses with insertions at either site in the α1 α-helical coiled-coil domain but not to wild-type rsT1L. These data indicate that the HIV-1 2F5 epitope retains native conformation in the context of the reovirus σ1 protein.

Figures 7A, 7B, 7C:
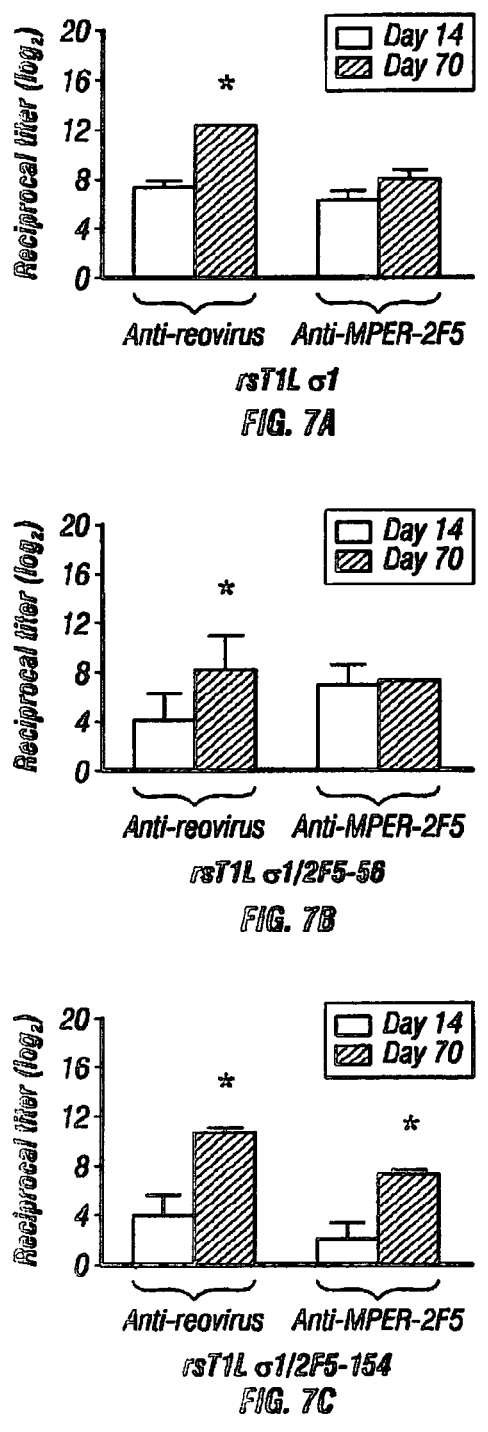

To determine whether REO-MPER vectors elicit MPER-specific humoral immune responses, the inventors inoculated BALB/c mice perorally with $10^7$ PFU of wild-type rsT1L, rsT1L/σ1 2F5-56, or rsT1L/σ1 2F5-154. Booster doses were administered 21 and 42 days following the initial immunization. Blood was collected on the day of inoculation (day 0) and on days 14 and 70 post-inoculation. Pre- and post-immunization serum samples were tested for the presence of reovirus-specific and MPER peptide-specific antibodies by FLISA. Antibodies specific for reovirus or MPER-specific peptide were not detected in any animal at day 0. As hoped, the inventors detected significant increases in reovirus-specific antibody titers from day 14 to day 70 in sera from mice inoculated with wild-type virus and both REO-MPER vectors (FIGS. 7A-C). Although sera from mice inoculated with wild-type rsT1L or rsT1L/σ1 2F5-56 did not display increases in peptide-specific anti-MPER antibodies during the observation interval (FIGS. 7A and 7B), the inventors did detect significant increases in anti-MPER antibodies in sera from mice inoculated with rsT1L/σ1 2F5-154 (FIG. 7C). The findings are encouraging and suggest that REO-MPER vectors stimulate the production of HIV-1 epitope-specific humoral immune responses in a manner dependent on the placement of MPER sequences in σ1.

Example 2

Future Studies

Recombinant reoviruses are ideal vectors to deliver antigens to the intestinal mucosa. Reoviruses are enteric viruses that replicate in intestinal epithelial cells, migrate to the GALT, and elicit robust mucosal and systemic immune responses (Virgin et al., 1997). These viruses are readily propagated in cell culture and naturally attenuated in humans (Liemann et al., 2002). Thus, recombinant reovirus vectors are well-suited for delivery of protective HIV-1 epitopes to the GALT for induction of mucosal and systemic immune responses.

Most humans become infected with reovirus in the first decade of life and develop reovirus-specific IgA (Selb and Weber, 1994) and IgG (Tai et al., 2005; Selb and Weber, 1994) antibodies. Despite this seropositivity, human subjects enrolled in clinical trials to evaluate reovirus as an oncolytic agent experience a boost in both humoral (Vidal et al., 2008) and cell-mediated (White et al., 2008) reovirus-specific immune responses. These observations suggest that a reovirus-based HIV-1 vaccine will induce HIV-1-specific antibody responses even in the face of preexisting immunity to reovirus, much in the way that the presence of neutralizing antibodies to poliovirus does not impair the capacity of recombinant poliovirus vectors to elicit vaccine-specific immunity (Mandl et al., 2001). Thus, a reovirus-based vaccine should be immunogenic in persons with prior reovirus exposure.

MPER sequences are conserved across HIV-1 subtypes (Montero et al., 2008; Zwick et al., 2005) and mediate an essential function in fusion of viral and cellular membranes to allow viral entry (Montero et al., 2008; Frey et al., 2008). Neutralizing mAbs 2F5, 4E10, and Z13 bind to the MPER and prevent infection by blocking membrane fusion (Montero et al., 2008). In passive immunization studies, MPER-specific neutralizing mAbs protect rhesus macaques against lethal SHIV mucosal challenge (Hessen et al., 2010). Thus, the MPER is an attractive target for vaccine design. In the proposed experiments, MPER sequences will be engineered into α-helical regions of σ1, σ3, or both proteins to develop replication-competent reovirus-based HIV-1 vaccines.

Reovirus attachment protein σ1 is a filamentous trimer ~480 Å in length with distinct head-and-tail morphology (Chappell et al., 2002; Furlong et al., 1988; Fraser et al., 1990) (FIG. 4). The σ1 tail folds into an extended region of α-helical coiled coil that stabilizes the trimer (Chappell et al., 2002; Nibert et al., 1990; Fraser et al., 1990). Like other α-helical regions, the α-helical coiled coil in a1 is formed by recurring sets of seven amino acids called heptad repeats (Dutch et al., 2000). There are 25 heptad repeats in the α-helical coiled-coil region of strain T1L σ1, spanning amino acid residues 7 to 181 (Nibert et al., 1990). The MPER assumes an α-helical secondary structure (Montero et al., 2008) similar to that predicted for the σ1 tail. The inventors hypothesize that replacement of α-helical regions of σ1 with antigenic α-helical regions of the MPER will yield a recombinant reovirus vaccine vector capable of inducing HIV-1 neutralizing antibody responses.

Reovirus outer-capsid protein σ3 is tightly associated with the μ1 protein on the surface of the virion capsid (Dryden et al., 1993; Liemann et al., 2002). The σ3 protein is proteolytically removed during viral disassembly in endosomes (Sturzenbecker et al., 1987; Ebert et al., 2002), which allows the conformational rearrangements in μ1 required for endosomal membrane penetration (Danthi et al., 2008; Chandran et al., 2002; Chandran et al., 2003). The structure of σ3 reveals a bi-lobed molecule composed of a virion-proximal small lobe that articulates with µ1 and a virion-distal large lobe that is exposed to solvent (Liemann et al., 2002) (FIG. 8). There are three α-helices in each lobe, and a large central α-helix bridges the small and large lobes of the protein (Liemann et al., 2002; 011 and et al., 2001). An α-helix comprised of amino acid residues 117 to 123 in the large lobe at the tip of β3 forms the epitope bound by σ3-specific mAb 4F2 (Nason et al., 2001), indicating that this region of σ3 is immunogenic. The inventors hypothesize that reovirus vectors engineered to display MPER sequences in place of the mAb 4F2 epitope α-helix will allow the MPER to retain native conformation and thus elicit MPER-specific humoral immune responses. In support of this idea, an adenovirus vector that displays the core mAb 2F5-binding epitope in hexon hypervariable region 5 elicits broadly neutralizing HIV-1-specific antibody responses following intramuscular immunization of mice (Ura et al., 2009).

Recombinant reovirus vectors that display MPER epitopes as chimeric σ1 or σ3 proteins will be used to immunize rabbits to assess induction of HIV-1-specific humoral immune responses. Humoral immune responses in mice following peroral and intramuscular inoculation with MPER-expressing reovirus vectors will be compared. Also, the inventors will evaluate an immunization schedule that employs sequential peroral and intramuscular inoculation. These experiments will test the hypothesis that recombinant reoviruses expressing MPER sequences elicit neutralizing HIV-1-specific antibodies in rabbits. These studies also will facilitate selection of MPER-expressing reovirus vectors for immunogenicity testing in non-human primates.

Figure 9:
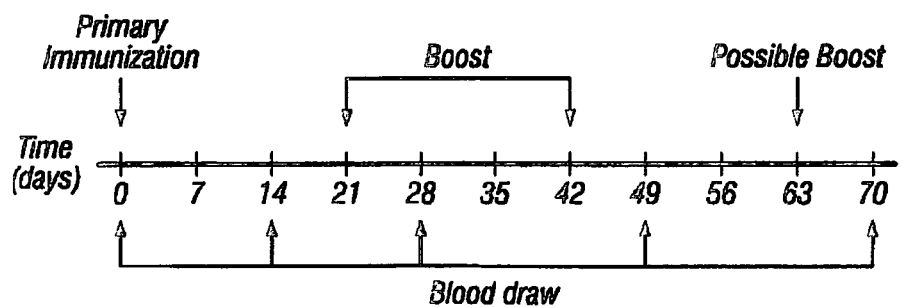
FIG. 9. Immunization of mice with MPER-expressing reovirus vectors. Mice will be inoculated perorally or intramuscularly with recombinant MPER-expressing reovirus or wild-type rsT1L vector control on days 0, 21, 42, and possibly 63 (black arrows). Blood will be collected on days 0, 14, 28, 49, and 70 (red arrows) for analysis of MPER-specific humoral immune responses.

New Zealand white rabbits will be used for the immunization studies proposed in this specific aim. Groups of eight 12-week-old, reovirus-seronegative New Zealand white rabbits will be inoculated either perorally or intramuscularly with $10^7$ PFU of recombinant MPER-expressing reovirus vectors or wild-type rsT1L as a negative control (FIG. 9). Animals will receive booster inoculations on days 21 and 42 by the same route. Other groups of eight rabbits will be inoculated perorally with either MPER-expressing reovirus vectors or wild-type rsT1L and boosted on days 21 and 42 by intramuscular inoculation. Blood, fecal samples, and vaginal lavages will be collected on days 0 (the time of initial inoculation), 14, 28, 49, and 70. Serum will be separated from the blood and stored in aliquots at −70° C. for further analysis. All other samples also will be stored at −70° C. for further analysis. Animals may receive an additional booster inoculation on day 63 depending on the strength of the HIV-1-specific immune responses.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

IX. References

The following references, to the extent that they provide exemplary procedural or other details supplementary to those set forth herein, are specifically incorporated herein by reference:

U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,945,100
U.S. Pat. No. 5,981,274
U.S. Pat. No. 5,994,624
U.S. Pat. No. 6,703,232
U.S. patent Ser. No. 11/960,357
Antar et al., *Cell Host Microbe.*, 5:59-71, 2009.
Armstrong et al., *Virology*, 138:37, 1984.
Baer and Dermody, *J. Virol.*, 71:4921-4928, 1997.
Baker et al., *Mol. Cell*, 3:309-319, 1999.
Barton et al., *Cell*, 104:441-451, 2001b.
Barton et al., *J. Biol. Chem.*, 276:2200-2211, 2001a.
Bosch et al., *Proc. Natl. Acad. Sci. USA*, 101:8455-8460, 2004.
Bullough et al., *Nature*, 371:37-43, 1994.
Campbell et al., *J. Virol.*, 79:7967-7978, 2005.
Chandran and Nibert, *Trends Microbiol.*, 11:374-382, 2003.
Chandran et al., *J. Virol.*, 76:9920-9933, 2002.
Chandran et al., *J. Virol.*, 77:13361-13375, 2003.
Chappell et al., *EMBO J.*, 21:1-11, 2002.
Chen and Okayama, *Mol. Cell Biol.*, 7(8):2745-2752, 1987.
Connolly et al., *J. Virol.*, 74:2981-2989, 2000.
Danthi et al., *J. Virol.*, 82:161-172, 2008.
Dryden et al., *J. Cell Biol.*, 122:1023-1041, 1993.
Dutch et al., *Biosci. Rep.*, 20:597-612, 2000.
Ebert et al., *J. Biol. Chem.*, 277:24609-24617, 2002.
Ehrlich et al., *Cell*, 118:591-605, 2004.
Eiraku et al., *J. Virol.*, 70:1481-1492, 1996.
Fechheimer, et al., *Proc Natl. Acad. Sci. USA*, 84:8463-8467, 1987.
Fields et al., *J. Mol. Med.*, 74:673-683, 1996.
Fleeton et al., *J. Exp. Med.* 200:235-245, 2004.
Fraley et al., *Proc. Natl. Acad. Sci. USA*, 76:3348-3352, 1979.
Fraser et al., *J. Virol.*, 64:2990-3000, 1990.
Frey et al., *Proc. Natl. Acad. Sci. USA*, 105:3739-3744, 2008.
Furlong et al., *J. Virol.*, 62:246-256, 1988.
Gentsch and Pacitti, *J. Virol.*, 56:356, 1985.
Giordano et al., *Pediatr. Infect. Dis. J.*, 21:880-882, 2002.
Gopal, *Mol. Cell Biol.*, 5:1188-1190, 1985.
Graham and Van Der Eb, *Virology*, 52:456-467, 1973.
Guglielmi et al., *Curr. Top. Microbiol. Immunol.*, 309:1-38, 2006.

Harland and Weintraub, *J. Cell Biol.*, 101(3):1094-1099, 1985.
Hermann et al., *Pediatr. Infect. Dis. J.*, 23:373-375, 2004.
Hessell et al., *J. Virol.*, 84(3):1302-13, 2010.
Jackson and Muldoon, *J. Infect. Dis.*, 128:811, 1973.
Johansson et al., *J. Exp. Med.*, 204:1349-1358, 2007.
Kaeppler et al., *Plant Cell Reports*, 9:415-418, 1990.
Kaneda et al., *Science*, 243:375-378, 1989.
Kato et al, *J. Biol. Chem.*, 266:3361-3364, 1991.
Kobayashi et al., *Cell Host Microbe*, 1:147-157, 2007.
Kobayashi et al., *Virology*, 398(2):194-200, 2010.
Kobe et al., *Proc. Natl. Acad. Sci. USA*, 96:4319-4324, 1999.
Liemann et al., *Cell*, 108:283-295, 2002.
Liu et al., *J. Cell Sci.*, 113:2363-2374, 2000.
London et al., *J. Exp. Med.*, 165:830-847, 1987.
Maginnis et al., *J. Virol.*, 80:2760-2770, 2006.
Major Cuff, *J. Virol.*, 70:5968-5974, 1996.
Mandl et al., *J. Virol.* 75:622-627, 2001.
Martin-Padura et al., *J. Cell Biol.*, 142:117-127, 1998.
Matthews et al., *J. Virol.*, 74:5911-5920, 2000.
Miller et al., *J. Virol.*, 81:141-149, 2007.
Montero et al., *Microbiol. Mol. Biol. Rev.*, 72:54-84, 2008.
Muster et al., *J. Virol.*, 67:6642-6647, 1993.
Nabel et al., *Science*, 244(4910):1342-1344, 1989.
Nason et al., *J. Virol.*, 75:6625-6634, 2001.
Neutra, *J. Infect. Dis.*, 179(Suppl 3):S441-3, 1999.
Nibert and Schiff, In: *Reoviruses and their replication*, Fields Virology, Knipe and Howley (Eds.), Philadelphia, Lippincott Williams & Wilkins, pp. 1679-1728, 2001.
Nibert et al., *J. Virol.*, 64:2976-2989, 1990.
Nicolau and Sene, *Biochim. Biophys. Acta*, 721:185-190, 1982.
Nicolau et al., *Methods Enzymol.*, 149:157-176, 1987.
Odegard et al., *J. Virol.*, 78:8732-8745, 2004.
O'Donnell et al., *Int. Rev. Immunol.*, 22:477-503, 2003.
O'Donnell et al., *J. Clin. Invest.*, 115:2341-2350, 2005.
O'Donnell et al., *J. Virol.*, 80:1077-1086, 2006.
Olland et al., *EMBO J*, 20:979-989, 2001.
Omirulleh et al., *Plant Mol. Biol.*, 21(3):415-428, 1993.
Organ and Rubin, D. H. Pathogenesis of reovirus gastrointestinal and hepatobiliary disease. *Curr. Top. Microbiol. Immunol.* 233:67-83, 1998.
Parker et al., *J. Virol.*, 75:10906-10911, 2001.
Paul et al. *Virology*, 172:382-385, 1989.
PCT Appln. WO 94/09699
PCT Appln. WO 95/06128
Potrykus et al., *Mol. Gen. Genet.*, 199(2):169-177, 1985.
Potter et al., *Proc. Natl. Acad. Sci. USA*, 81:7161-7165, 1984.
Remington's Pharmaceutical Sciences, 15$^{th}$ Ed., 1035-1038 and 1570-1580, 1990.
Rippe, et al., *Mol. Cell Biol.*, 10:689-695, 1990.
Sabin, *Science*, 130:1387-1389, 1959.
Schiff et al., *In Fields Virology*, Knipe and Howley (Eds.), PA, Lippincott Williams & Wilkins, 1853-1915, 2007.
Selb and Weber, *J. Virol. Methods*, 47:15-25, 1994.
Shen et al., *J. Virol.*, 83:3617-3625, 2009.
Stanley, In: *Comparative Diagnosis of Viral Diseases*, 385-421, Academic Press, NY, 1974.
Sturzenbecker et al., *J. Virol.*, 61:2351-2361, 1987.
Tai et al., *J. Infect. Dis.*, 191:1221-1224, 2005.
Tripet et al., *J. Biol. Chem.*, 279:20836-20849, 2004.
Tur-Kaspa et al., *Mol. Cell Biol.*, 6:716-718, 1986.
Tyler et al., *J. Infect. Dis.*, 189:1664-1675, 2004.
Tyler et al., *J. Virol.*, 67:3446-3453, 1993.
Ura et al., *J. Gene Med.*, 11:139-149, 2009.
Vidal et al., *Clin. Cancer. Res.*, 14:7127-7137, 2008.
Virgin et al., In: *Viral Pathogenesis*, Nathanson (Ed.), NY, Lippincott-Raven, 669-699, 1997.
Virgin et al., *J. Virol.*, 65:6772-6781, 1991.
Weissenhorn et al., *Mol. Cell*, 2:605-616, 1998b.
Weissenhorn et al., *Proc. Natl. Acad. Sci. USA*, 95:6032-6036, 1998a.
White et al., *Gene Ther.*, 15:911-920, 2008.
Wilson et al., *Science*, 244:1344-1346, 1989.
Wolf et al., *Science*, 212:471-472, 1981.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Xu et al., *Biochem. Biophys. Res. Commun.*, 315:664-670, 2004.
Zwick et al., *J. Virol.*, 75:10892-10905, 2001a.
Zwick et al., *J. Virol.*, 75:12198-12208, 2001b.
Zwick et al., *J. Virol.*, 79:1252-1261, 2005.

What is claimed is:

1. A modified reovirus σ1 protein comprising a first α-helical antigenic epitope from a non-reovirus antigen inserted into an α-helical region of said protein.

2. The modified reovirus σ1 protein of claim 1, wherein said first epitope replaces one or more heptad repeats in said α-helical region of said protein.

3. The modified reovirus σ1 protein of claim 1, wherein said first epitope is a viral epitope.

4. The modified reovirus σ1 protein of claim 1, wherein said first epitope is a bacterial epitope.

5. The modified reovirus σ1 protein of claim 1, wherein said first epitope is a fungal epitope or a parasite epitope.

6. A reovirus vector encoding a reovirus σ1 protein comprising a first α-helical antigenic epitope from a non-reovirus antigen inserted into an α-helical region of said protein.

7. A reovirus particle comprising a vector encoding a reovirus σ1 protein comprising a first α-helical antigenic epitope from a non-reovirus antigen inserted into α-helical region of said protein.

8. The reovirus particle of claim 7, wherein said first epitope replaces one or more heptad repeats in said α-helical region of said protein.

9. The reovirus particle of claim 7, wherein said first epitope is a viral epitope, a bacterial epitope, or a fungal epitope.

10. The reovirus particle of claim 7, further comprising a second copy of said first epitope in said α-helical region.

11. The reovirus particle of claim 10, wherein said second copy replaces one or more heptad repeats in said α-helical region of said protein.

12. A method of inducing an immune response in a subject comprising administering to said subject a modified reovirus σ1 protein comprising a first α-helical antigenic epitope from a non-reovirus antigen inserted into an α-helical region of said protein, a reovirus vector encoding said modified reovirus σ1 protein, or a viral particle comprising a vector encoding said modified reovirus σ1 protein.

13. The method of claim 12, wherein said first epitope replaces one or more heptad repeats in said α-helical region of said protein.

14. The method of claim 12, wherein said first epitope is a viral epitope.

15. The method of claim 12, wherein said first epitope is a bacterial epitope.

16. The method of claim 12, wherein said first epitope is a fungal epitope or a parasite epitope.

17. The method of claim 12, wherein said α-helical region comprises a second epitope from a non-reovirus antigen, wherein said second epitope replaces one or more heptad repeats in said α-helical region of said protein.

18. The method of claim 12, wherein said modified reovirus σ1 protein is administered.

19. The method of claim 12, wherein said vector encoding said modified reovirus σ1 protein is administered.

20. The method of claim 12, wherein said viral particle comprising a vector encoding said modifies reovirus σ1 protein is administered.

21. A method of expressing an epitope in a subject comprising administering to said subject a modified reovirus σ1 protein comprising a first α-helical antigenic epitope from an antigen inserted into an α-helical region of said protein.

* * * * *